US010326030B2

(12) United States Patent
Yu

(10) Patent No.: US 10,326,030 B2
(45) Date of Patent: Jun. 18, 2019

(54) OPTICAL SENSOR AND MANUFACTURING METHOD THEREOF

(71) Applicant: PERSONAL GENOMICS, INC., Grand Cayman (KY)

(72) Inventor: Teng-Chien Yu, Hsinchu (TW)

(73) Assignee: PERSONAL GENOMICS, INC., Grand Cayman (KY)

( * ) Notice: Subject to any disclaimer, the term of this patent is extended or adjusted under 35 U.S.C. 154(b) by 0 days.

(21) Appl. No.: 14/695,675

(22) Filed: Apr. 24, 2015

(65) Prior Publication Data

US 2015/0311376 A1 Oct. 29, 2015

Related U.S. Application Data

(60) Provisional application No. 61/984,389, filed on Apr. 25, 2014.

(51) Int. Cl.
| | | |
|---|---|---|
| *H01L 31/0232* | (2014.01) | |
| *G01N 21/77* | (2006.01) | |
| *G01N 21/64* | (2006.01) | |
| *G02B 6/42* | (2006.01) | |

(Continued)

(52) U.S. Cl.
CPC ..... *H01L 31/02327* (2013.01); *G01N 21/648* (2013.01); *G01N 21/7703* (2013.01); *G02B 6/4204* (2013.01); *H01L 27/1464* (2013.01); *H01L 27/14625* (2013.01); *H01L 27/14629* (2013.01); *H01L 27/14687* (2013.01); *H01L 31/1013* (2013.01); *G01N 2021/7716* (2013.01); *G01N 2021/7786* (2013.01)

(58) Field of Classification Search
CPC ...... H01L 31/111; H01L 31/11; G01N 21/648

USPC .............................................. 422/82.11, 82.09
See application file for complete search history.

(56) References Cited

U.S. PATENT DOCUMENTS

| | | | |
|---|---|---|---|
| 6,646,318 B1 * | 11/2003 | Hopper | ............. H01L 27/14647 257/188 |
| 7,175,811 B2 | 2/2007 | Bach et al. | |
| 8,471,230 B2 | 6/2013 | Zhong et al. | |

(Continued)

FOREIGN PATENT DOCUMENTS

| | | |
|---|---|---|
| JP | 2013-98534 | 5/2013 |
| JP | 2013-522605 A | 6/2013 |

(Continued)

OTHER PUBLICATIONS

Office Action from the corresponding Taiwanese application, dated Jul. 1, 2016, 8 pages.

(Continued)

*Primary Examiner* — Nishath Yasmeen
(74) *Attorney, Agent, or Firm* — Muncy, Geissler, Olds & Lowe, P.C.

(57) ABSTRACT

Some embodiments of the present disclosure provide an optical sensor. The optical sensor includes a semiconductive block having a front side and a back side, a wave guide region, and a light sensing region. The wave guide region is positioned over the back side of the semiconductive block and having a core layer. The wave guide region is configured to guide an incident light. The light sensing region is positioned in the semiconductive block, having a multi-junction photodiode. The light sensing region is configured to sense emission lights from the wave guide region.

13 Claims, 32 Drawing Sheets

(51) Int. Cl.
*H01L 27/146* (2006.01)
*H01L 31/101* (2006.01)

(56) References Cited

U.S. PATENT DOCUMENTS

| | | | | |
|---|---|---|---|---|
| 2004/0252943 | A1* | 12/2004 | Schilling | G02B 6/34 385/37 |
| 2006/0181712 | A1* | 8/2006 | Degertekin | G01B 11/02 356/505 |
| 2007/0218613 | A1* | 9/2007 | Lee | H01L 27/1463 438/197 |
| 2008/0180673 | A1 | 7/2008 | Sampas et al. | |
| 2008/0203452 | A1* | 8/2008 | Moon | H01L 27/14603 257/292 |
| 2009/0200625 | A1* | 8/2009 | Venezia | H01L 27/1463 257/432 |
| 2011/0223590 | A1* | 9/2011 | Chiou | C12Q 1/6869 435/6.1 |
| 2011/0306143 | A1* | 12/2011 | Chiou | B82Y 15/00 436/94 |
| 2012/0082016 | A1* | 4/2012 | Komura | B82Y 20/00 369/13.33 |
| 2012/0156100 | A1* | 6/2012 | Tsai | G01N 21/6428 422/82.08 |
| 2012/0298841 | A1 | 11/2012 | Yamashita et al. | |
| 2013/0105945 | A1* | 5/2013 | Tsai | H01L 27/14607 257/610 |
| 2013/0328151 | A1* | 12/2013 | Kao | H01L 27/14636 257/443 |
| 2013/0338010 | A1 | 12/2013 | Turner et al. | |

FOREIGN PATENT DOCUMENTS

| | | |
|---|---|---|
| JP | T-2013-524174 | 6/2013 |
| TW | 200832688 | 8/2008 |
| TW | 200832688 A | 8/2008 |
| TW | 201144793 | 12/2011 |
| TW | 201144793 A | 12/2011 |
| TW | 201318156 | 5/2013 |
| WO | WO 97/06422 A1 | 2/1997 |
| WO | WO9706422 A1 | 2/1997 |

OTHER PUBLICATIONS

Office Action dated Jul. 3, 2017 issued in counterpart CN patent application No. 201510202657.0, the search report and partial English translation (8 pages).

Eric E. Schadt, Steve Turner. Andrew Kasarskis, "A window into third-generation sequencing", Human Molecular Genetics, 2010, vol. 19, Review Issue 2, Sep. 17, 2010, R227-R240.

* cited by examiner

OPTICAL SENSOR AND MANUFACTURING METHOD THEREOF

FIELD

The present disclosure relates to an optical sensor and a method of manufacturing the same.

BACKGROUND

Optical sensors are widely used in various applications and products, such as cameras, scanners, photocopiers, etc. Optical sensors used in various fields of technology are designed with different purposes. Different types of improvements are applied for suitable fields of technology.

To improve performance and size reduction of optical sensors, various designs of optical sensors are employed. One way to evaluate the performance is by measuring the quantum efficiency of optical sensors. Quantum efficiency is a percentage of photons hitting an optical sensor that produces charge carriers. It is a measurement of an optical sensor's electrical sensitivity to light.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
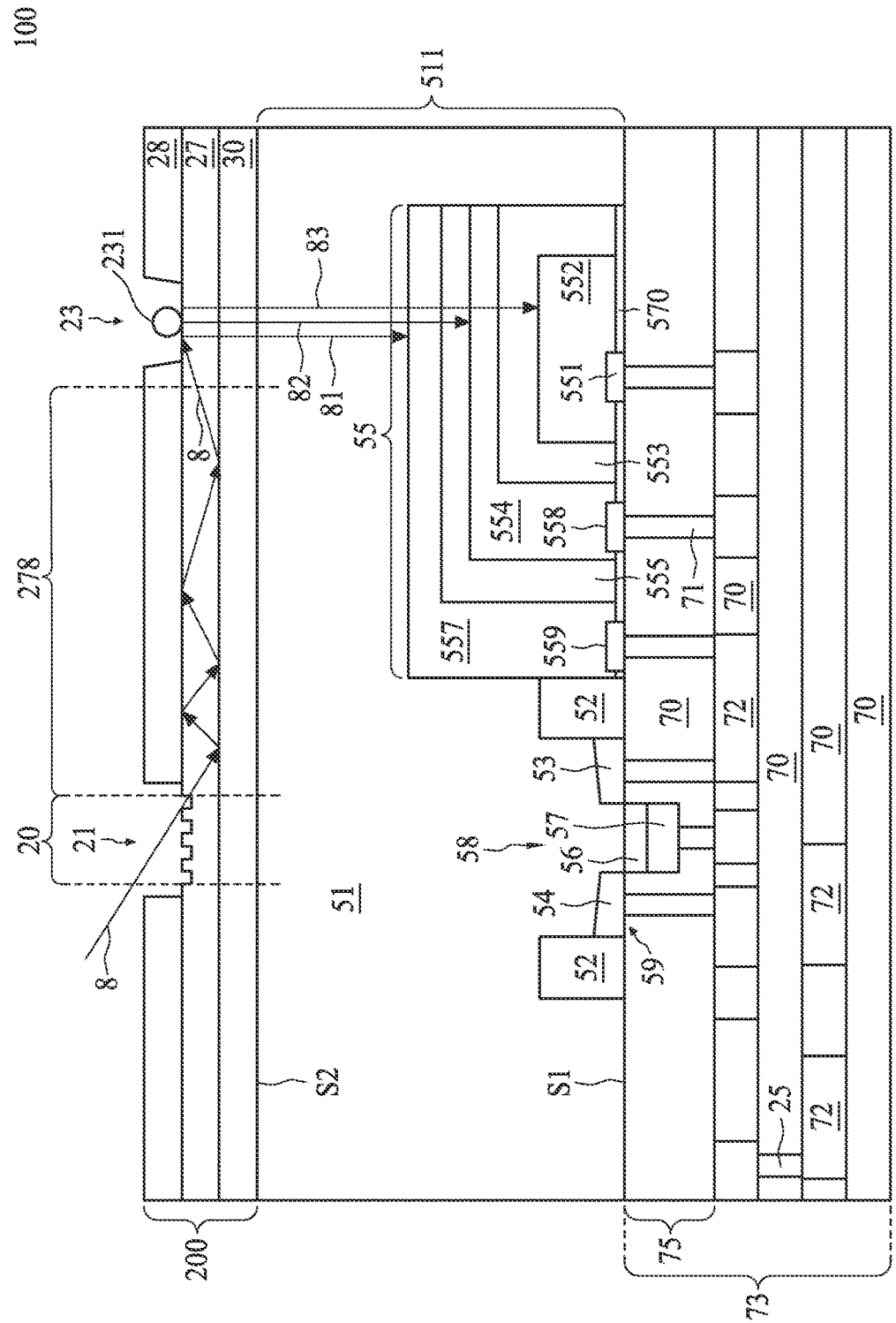
FIGS. 1-4 are cross-sectional views of optical sensors, in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

For a front-side illuminated image sensor such as a front-side illuminated optical bio sensor, light emitted from the bio specimen travels through conductive material, such as metallic interconnects and dielectric materials surrounding the interconnects, to reach a light sensing region designed to sense the emitted light. The metallic interconnects can block or scatter a portion of the light and inevitably attenuate the intensity of the light, rendering low sensitivity.

By placing the photodiode between the bio specimen and the interconnects, optical elements are separated from electrical elements of the image sensor. Light from the specimens is unblocked by the metallic interconnects such that the loss of the light is decreased and high quantum efficiency can be achieved. With the light sensing region closer to the specimens, the light sensing region is exposed to greater intensity of the light to be detected.

FIG. 1 illustrates an optical sensor 100 including an interconnection region 73, a wave guide region 200 and a light sensing region 55. In some embodiments, the wave guide region 200 is above the interconnection region 73 and/or light sensing region 55. A light sensing region 55 is between the wave guide region 200 and the interconnection region 73. The light sensing region 55 is under the wave guide region 200 and above the interconnection region 73. A semiconductive block 511 includes epitaxy layers in an epitaxy region 51. In some embodiments, the semiconductive block 511 includes a layer made of semiconductive material. The light sensing region 55 is in the epitaxy region 51. The semiconductive block 511 includes a front side S1 and a back side S2. In some embodiments, the wave guide region 200 is over the back side S2 of the semiconductive block 511. The interconnection region 73 is in proximity to or in contact with the front side S1.

Referring to FIG. 1, a light 8 incidents upon a grating structure 21 at an insert portion 20. In some embodiments, the dielectric layer 28 includes a recess over the grating structure 21 such that the grating structure 21 in the dielectric layer 27 is exposed and the light 8 incident upon the dielectric layer 27 directly. In some embodiments, the light 8 includes a range of wavelengths from around 450 nanometers to around 550 nanometers. The light 8 travels from the insert portion 20 and propagates in a wave guide portion 278. The light 8 is mostly confined within a dielectric layer 27. The light 8 can be a laser light traveling into the wave guide region 200. The light 8 can be an incident light propagating in the dielectric layer 27. In some embodiments, the dielectric layer 27 is a core layer 27 of the wave guide region 200. The wave guide region 200 guides the light 8 from a light source (not shown) through the core layer 27 of the wave guide region 200. The light 8 reaches a sample holding portion 23 of the wave guide region 200 and illuminates on a specimen 231. Since the light 8 is confined in the core layer 27 of the wave guide region 200, the light 8 by itself may not positively interact with the specimen 231 disposed in the sample holding portion 23. In some embodiments, evanescent waves of the light 8 couple with the specimen 231 above the core layer 27. In response to the evanescent wave of the light 8, the specimen 231 emits a light of a certain wavelength, such as fluorescent light. The wavelength of the emitted fluorescent light, for example, can be a characteristic of a material in the specimen 231. For example, in some embodiments, the specimen 231 emits a different wavelength of fluorescent light, such as a light 81, a light 82, and a light 83. The lights 81, 82, and 83 pass through a filter layer 30 near a bottom of the wave guide region 200. Alternatively stated, the filter layer 30 is transparent to the wavelength emitted from the specimen 231. In some embodiments, the lights 81, 82, and 83 travel through the filter layer 30 toward the epitaxy region 51.

In some embodiments, the filter layer 30 can be a filter blocking a range of predetermined wavelengths. In some embodiments, the filter layer 30 is designed to filter a wavelength of the light 8 smaller than or greater than a wavelength of the lights 81, 82, and 83 such that the filter layer 30 is transparent to the lights 81, 82, and 83 but opaque to the light 8. The lights 81, 82, and 83 pass the epitaxy region 51 and enter into the light sensing region 55.

The light sensing region 55 senses lights such as emission lights from the wave guide region 200. In the light sensing region 55, the emission lights such as lights 81, 82, and 83 are absorbed at a different region 552, 554, and 557 respectively. Specifically, the lights 81, 82, and 83 are absorbed at junctions between the region 552 and the region 553, the region 554 and the region 555, and the region 557 and the epitaxy region 51 respectively. In some embodiments, the region 557 is referred to as a deep well region 557. In some embodiments, the region 554 is referred to as a middle well region 554, and the region 552 is referred to as a shallow well region 552. A quantum efficiency of each region 552, 554, 557 is different for different wavelengths of light. For example, the quantum efficiency near the region 557 is larger for the wavelength of the light 81 than for another wavelength of light, such as the wavelength of the light 82 or 83. Most of the light 81 is absorbed near the region 557. In some embodiments, wavelengths of the light 81, 82, 83 are from shortest to longest in an increasing order respectively. In some embodiments, the light 81 can be from about 450 nm to about 550 nm, the light 82 can be from about 550 nm to about 650 nm, and the light 83 can be from about 650 nm to about 800 nm.

The light 81 is converted by a light sensing element in the region 552, 554, or 557 into data information. The light 81 absorbed in the region 557 converts to charge carriers in the region 557. In some embodiments, the charge carrier can be positive or negative. The charge carriers flow to a contact plug 551, 559 or 558 so as to transfer information about the characteristic of the specimen 231 to the circuitry in the interconnection region 73 for further processing and/or output.

The charge carrier is transferred through heavily doped regions 551, 558, 559 in each region 552, 554, and 557, respectively, to a first layer via 71. The first layer via in some embodiments may also function as a contact. For example, the charge carriers are transferred from the region 552 to the heavily doped region 551 within the region 552. In some embodiments, the heavily doped region 551 and the region 552 include a same type of dopant, such as a positive-type or a negative-type of dopant.

In some embodiments, the region 552, 554, or 557 is coupled to another semiconductive device, such as a transistor 59, through the heavily doped region 551, 558, or 559. In some embodiments, the heavily doped region 551, 558, or 559 is coupled to another semiconductive device, such as the transistor 59, through a contact 71 or interconnects 72. Data information is transferred from the transistor 59 to the circuitry in the interconnection region 73. The interconnection region 73 is coupled with the multi-junction photodiode in the light sensing region 55 near the front side S1. The multi-junction photodiode is proximate to the front side S1 with multiple junctions in contact with the front side S1. In some embodiments, multiple transistors 59 are coupled to multiple light sensing regions 55 so as to transfer various data information about specimens 231 in multiple sample holding portions 23. The transistor 59 is bordered at the front side S1. In some embodiments, other transistors in the optical sensor 100 are structured similarly to the transistor 59.

The transistor 59 is coupled to the light sensing element in the light sensing region 55 so as to transfer image data to the circuitry for further processing and/or output. In some embodiments, the light sensing element includes a light sensing diode. In some embodiments, the light sensing diode includes the region 557 and 555.

In some embodiments, a dielectric layer 28 is an upper cladding layer including a material, such as $SiO_2$. In some embodiments, the dielectric layer 27 is the core layer 27 including a material, such as $Ta_2O_5$ or SiON. In some embodiments, interconnects 72 or a via structure 25 may be composed of a material such as aluminum, copper, titanium nitride, tungsten, titanium, tantalum, tantalum nitride, nickel silicide, cobalt silicide, TaC, TaSiN, TaCN, TiAl, TiAlN, other suitable conductive materials, and/or combinations thereof.

In some other embodiments, the dielectric layer 28 is replaced by a covering layer. In some embodiments, the covering layer includes a metal or a metal oxide. The metal includes aluminum and the metal oxide includes aluminum dioxide. In some embodiments, a glass layer is between the covering layer and the core layer 27. The covering layer disposed over the core layer 27 includes a nanowell as the sample holding portion 23.

The light sensing region 55 is a multi-junction photodiode for detecting light of various wavelengths. In some embodiments, a semiconductive block 511 includes first conductive type dopants, such as positive type dopants, in epitaxy region 51. A region 557 includes second conductive type dopants, such as negative type dopants. A region 555 includes the first conductive type dopants. In some embodiments, a semiconductor layer, such as the region 555, is a well region. A region 554 includes the second conductive type dopants. A region 553 includes the first conductive type dopants. In some embodiments, the region 553 is a well region. A region 552 includes the second conductive type dopants. Conductive types of each semiconductor layer can be alternated as a design factor. Heavily doped regions 551, 558, or 559 include the second conductive type dopants. In some embodiments, a doping concentration of heavily doped regions 551, 559 or 558 is from around 10E18 to 10E21 atoms/$cm^3$. The heavily doped region 551, 558, or 559 is closer to the front side S1 than to the back side S2. In some embodiments, the heavily doped region 551, 558, or 559 is in contact with the front side S1.

The region 552, 553, 554, 555, or 557 includes a thin layer of a doping region 570. The doping region 570 is in contact with the front side S1. In some embodiments, the doping region 570 is thinner than the heavily doped region 551, 558, or 559. In some embodiments, a doping concentration of the doping region 570 is around 10E18 to 10E20 atoms/$cm^3$. In some embodiments, the doping region 570 includes a higher doping concentration than other regions in the light sensing region 55. The doping region 570 can avoid carrier diffusion to the exterior environment, such as to the interconnection region 73. The doping region 570 lowers a dark current by isolating surface defects near the front side S1.

In some embodiments, a doping concentration in some portions of the epitaxy region 51, and the region 552, 553, 554, 555, or 557, is from around 10E15 to 10E18 atoms/cm³. In some embodiments, the first conductive type dopants is the positive conductive type dopants such as boron. The epitaxy region 51 is a lightly doped epitaxy such that a doping concentration of the first conductive type dopants in the epitaxy region 51 is less than the predetermined doping concentration in other portions of the semiconductive block 511. In some embodiments, the epitaxy region 51 is composed of SiGe for the doping concentration of positive conductive type dopants. In some embodiments, the epitaxy region 51 is composes of SiC for the doping concentration of negative conductive type dopants. In some embodiments, the epitaxy region 51 includes a concentration profile of SiGe or SiC.

The regions 557, 554, or 552 include the second conductive type dopants, such as phosphorus, in predetermined doping concentrations. In some embodiments, the predetermined doping concentrations are substantially the same. In some embodiments, the predetermined doping concentrations are substantially greater than the doping concentrations of the first conductive type dopants in the epitaxy region 51.

The region 555 or 553 includes the first conductive type dopants, such as boron, in some predetermined doping concentrations. In some embodiments, the predetermined doping concentrations are substantially the same. The doping concentration of the first conductive type dopants in the region 555 or 553 is substantially greater than the predetermined doping concentrations of the second conductive type dopants in the region 557, 554, or 552.

In some embodiments, a portion of the region 557, 554, or 552 closer to the front side S1 includes a higher doping concentration than another portion of the region 557, 554, or 552 respectively. In other words, the regions 557, 554, or 552 may include a concentration gradient of the dopants within each region. The portion of the region 557, 554, or 552 closer to the heavily doped region 559, 558, or 551 serves as a terminal of the region 557, 554, or 552 for an outer connection. In some embodiments, the heavily doped region 559, 558, or 551 includes a material, such as a metal or other conductive materials.

The epitaxy region 51 includes isolation regions 52 in proximity to the front side S1. In some embodiments, the isolation region 52 is a shallow trench isolation (STI) feature or a local oxidation of silicon (LOCOS) feature. The isolation regions 52 define and isolate various elements or regions from each other in the epitaxy region 51 or in the semiconductive block 511. For example, the isolation regions 52 isolate adjacent light sensing regions 55 from each other, isolate the light sensing region 55 from the transistor 59, or isolate some components of the circuitry from each other, etc. In some embodiments, the isolation region 52 is made of a dielectric material.

The transistor 59 is disposed at the front side S1 of the epitaxy region 51. The transistor 59 includes a gate structure 58, a source region 53 and a drain region 54. The gate structure 58 includes a gate dielectric 56 and a gate electrode 57.

The gate dielectric 56 composes a high-k dielectric layer or combination thereof. The gate dielectric 56 is made of any suitable dielectric material, such as hafnium oxide (HfO) or hafnium silicon oxide (HfSiO).

The gate structure 58, the source region 53, and the drain region 54 of the transistor 59 are coupled to a plurality of first layer vias, or hereinafter referred to as a "contact" 71. The contacts 71 pass through the dielectric layer 70 such that the contacts 71 connect with some portions of the gate structure 58, the source region 53, or the drain region 54. The contacts 71 are in contact with a portion of the front side S1 below the source region 53, the drain region 54, or the light sensing region 55. In some embodiments, the contacts 71 and the dielectric layer 70 are in an inter-layer dielectric (ILD) layer 75. The ILD layer 75 is below the transistors 59 and the light sensing region 55. The transistor 59 is proximate to the light sensing region 55. The interconnection region 73 includes the transistor 59, the ILD layer 75, the dielectric layer 70, and the interconnects 72. For brevity, the via structure and the metal lines are generalized as interconnects in the present disclosure. The interconnection region 73 is below the front side S1.

Figure 2:
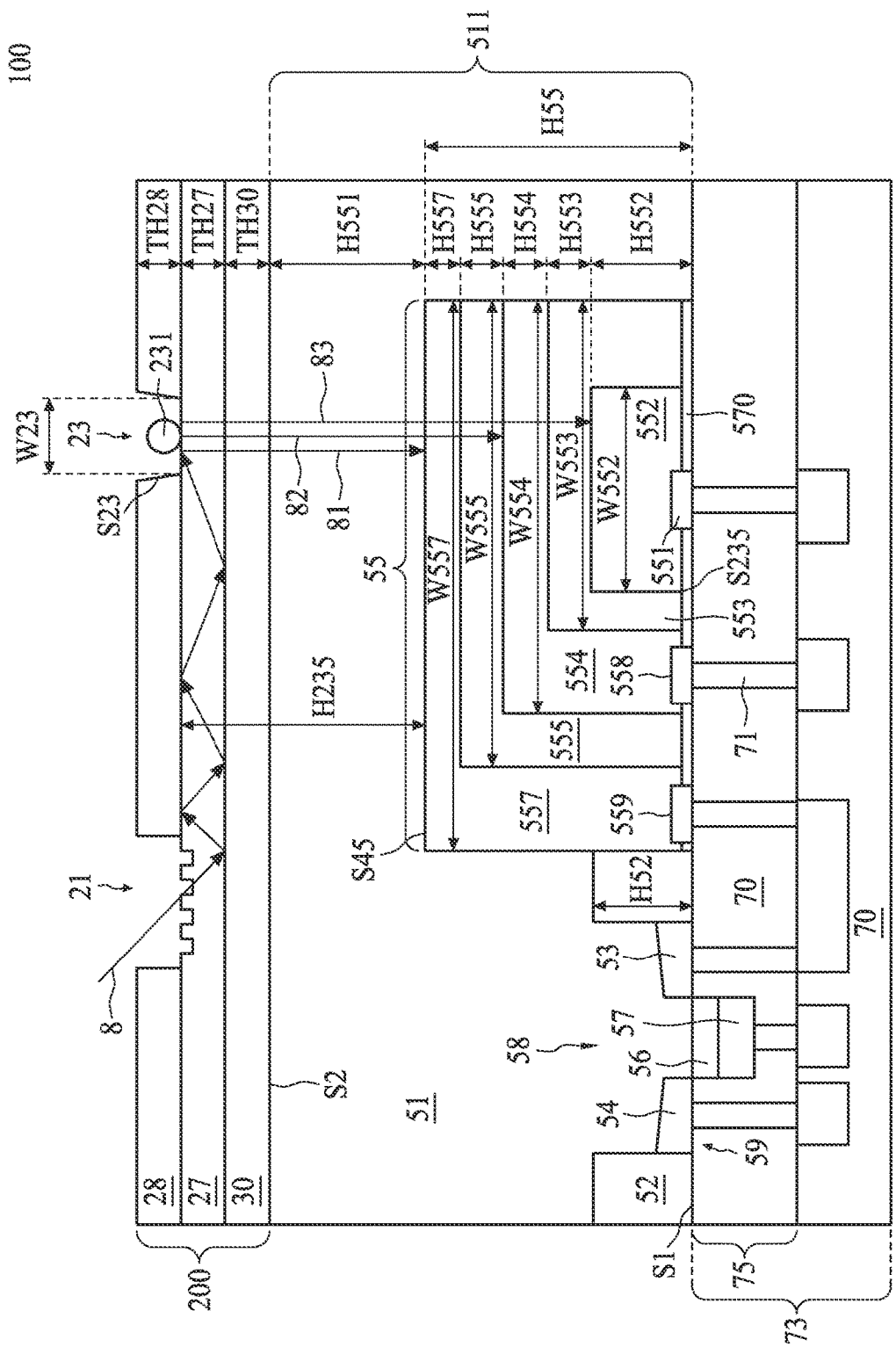

FIG. 2 illustrates various parameters in the optical sensor 100. In the wave guide region 200, a sample holding portion 23 is above the back side S2 by a predetermined distance. In some embodiments, the predetermined distance is a sum of a thickness TH27 and TH28. The dielectric layer 28 includes the thickness TH28. The dielectric layer 27 includes the thickness TH27. In some embodiments, the thickness TH27 is around 150 nanometers plus about 5 to 10 percent. In some embodiments, the filter layer 30 is between the back side S2 and the core layer 27. The filter layer 30 includes a thickness TH30. In some embodiments, the thickness TH30 is around 2 micrometers. In some embodiments, the filter layer 30 includes multiple stacks of some dielectric layers designed to filter different wavelengths of the light 8 such that the light 8 is prevented from entering into the epitaxy region 51. In some embodiments, the stacks of the dielectric layers include $SiO_2/Ta_2O_5$ in an alternating arrangement.

The sample holding portion 23 is a nanowell including a width W23. The sample holding portion 23 includes a height substantially equal to the thickness TH28 of the dielectric layer 28. In some embodiments, the thickness TH28 can be around 330 nanometers plus or minus about 10 percent. In some embodiments, a ratio between the thickness TH28 and the thickness TH27 is proximately around 2.

The ILD layer 75 is in contact with the front side S1 of the epitaxy region 51. An interface S45 is between the epitaxy region 51 and the light sensing region 55. The specimen 231 is proximately above the top surface of the light sensing region 55 by a predetermined height H235. The predetermined height H235 is proximately a sum of the thickness TH27, the thickness TH30, and the height H551. The height H551 is from the back side S2 to the interface S45 of the light sensing region 55.

The light sensing region 55 is between the back side S2 and the front side S1 of the semiconductive block 511. The light sensing region 55 includes a multi-junction photodiode. The multi-junction photodiode includes the semiconductor layers, such as regions 552, 553, 554, 555, and 557.

The light sensing region 55 includes a height H55 and a width W557. The height H55 is from the front side S1 to the interface S45 between the epitaxy region 51 and the region 557. The width W557 is a width of the region 557. In some embodiments, the height H551 is from around 0.2 micrometers to around 0.5 micrometers.

A sum of heights H551, H557, and H555 is a distance from the back side S2 to a junction between the region 555 and the region 554. In some embodiments, the sum is from around 0.5 micrometers to around 1.5 micrometers. Different wavelengths of the light 81, 82, or 83 have different penetration depths in the light sensing region 55. A sum of heights H551, H557, H555, H554, and H553 is a distance from the back side S2 to a junction between the region 553 and the region 552. In some embodiments, the sum is from around 2.5 micrometers to around 3 micrometers. A sum of the height H55 and the height H551 is proximately a height of the semiconductive block 511. In some embodiments, the height of the semiconductive block 511 is from around 2.5 micrometers to around 5 micrometers.

In some embodiments, the region 557, 555, or 554 includes a vertical portion and a horizontal portion. The horizontal portion is substantially parallel to the front side S1. The front side S1 is an interface between the dielectric layer 70 and the epitaxy region 51.

The interface between the epitaxy region 51 and the region 557 is a p-n junction. Some horizontal interfaces are p-n junctions between horizontal portions of the region 557 and the region 555, between horizontal portions of the region 555 and the region 554, between horizontal portions of the region 554 and the region 553, and between horizontal portions of the region 553 and the region 552. Some vertical interfaces are p-n junctions proximate to the transistor 59 between vertical portions of the region 557 and the region 555, between vertical portions of the region 555 and the region 554, between vertical portions of the region 554 and the region 553, and between vertical portions of the region 553 and the region 552. The light sensing region 55 is a multi-junction photodiode structure capable of sensing light of various wavelengths at different interfaces. Different wavelengths of light have different penetration depths in the light sensing region 55. The multi-junction photodiode includes multiple wavelength detection based on light absorption properties of silicon. For example, the region 552 surrounded by the region 553 is a first photodiode; the region 554 surrounded by the region 555 and the region 553 is a second photodiode; and the region 557 surrounded by the epitaxy region 51 is a third photodiode.

The light sensing region 55 is the multi-junction photodiode structure including regions 552, 553, 554, 555, and 557 at different depth from the sample holding portion 23 and is used for sensing different wavelength of light. Light with a longer wavelength is detected more by a photodiode located further from the sample holding portion 23, such as the third photodiode. Light with a shorter wavelength is detected more by a photodiode located closer to the sample holding portion 23, such as the first photodiode.

Figure 17:
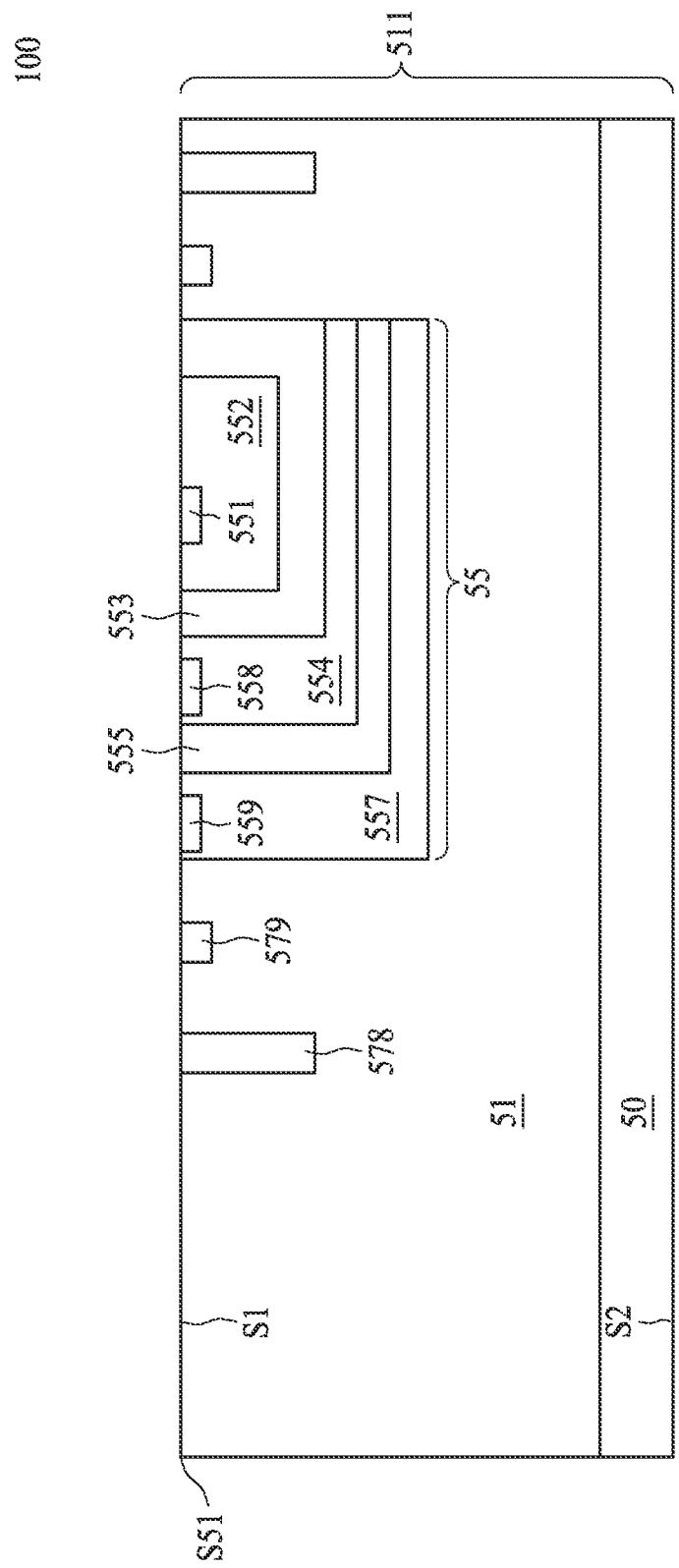

In some embodiments, structures of each region 552, 553, 554, 555, or 557 possess a common axis parallel to a measurement of the height H55, or orthogonal to the front side S1. In some embodiments, there are highly-doped regions 579, as shown in FIG. 17, of a high dopant concentration surrounding a periphery of the photodiode in the light sensing region 55 so as to prevent noise impact from outer circuits and cross-talk from other adjacent photodiodes. The highly-doped regions 579 lower some internal dark current of the photodiode.

Figure 3:
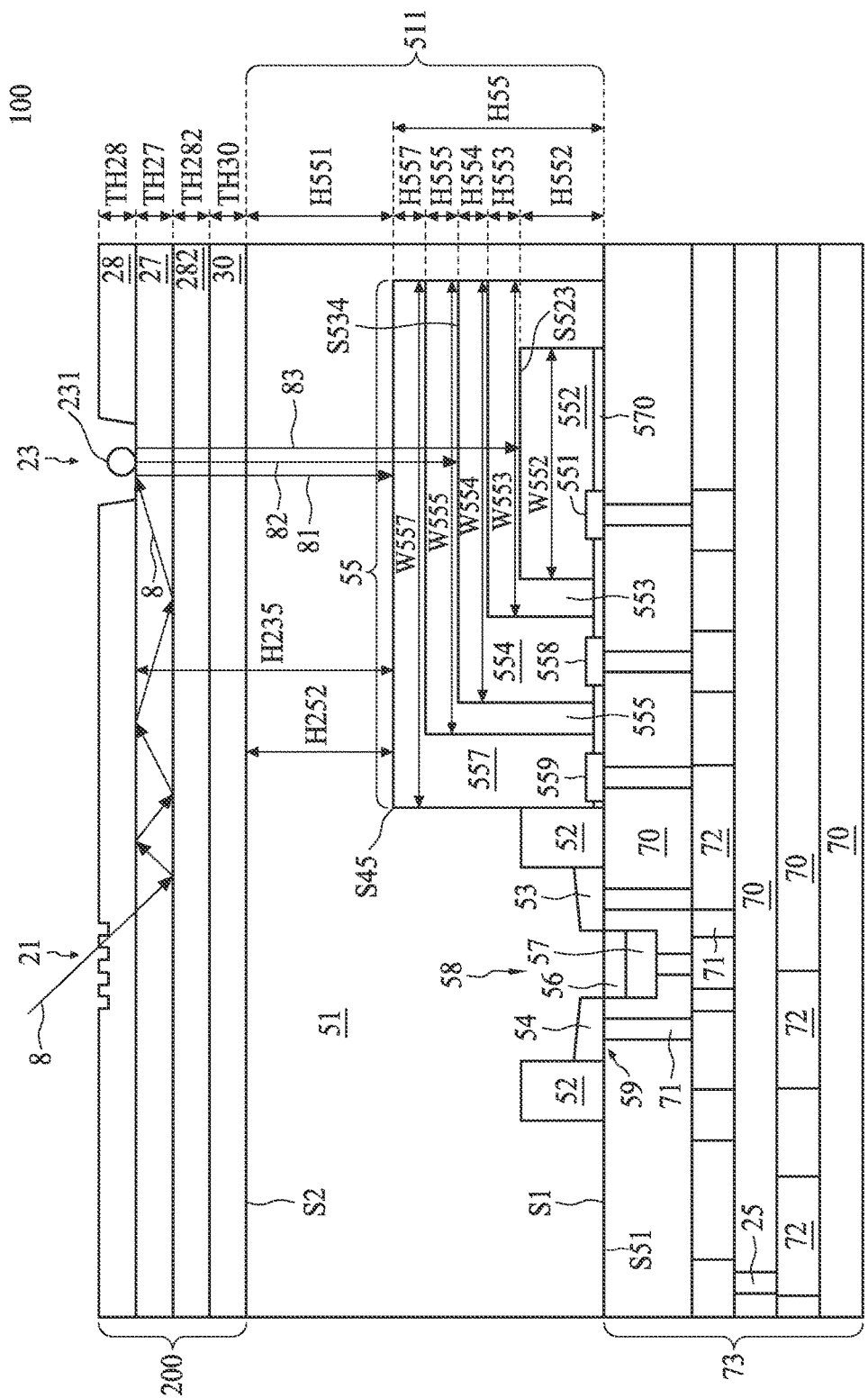

FIG. 3 is similar to FIG. 1, except that a dielectric layer 282 is added below the core layer 27. The differences are briefly discussed below.

The dielectric layer 282 below the core layer 27 includes a thickness TH282. The dielectric layer 282 is a lower cladding layer below the core layer 27. In some embodiments, the thickness TH282 is substantially greater than the thickness TH27 or TH28 such that the dielectric layer 282 can provide a support to hold the dielectric layer 27. In some embodiments, a distance from the sample holding portion 23 to the back side S2 is proximately a sum of thicknesses TH27, TH282, and TH30. The sum is around 3 micrometers. Instead of placing the interconnection region 73 between the wave guide region 200 and the light sensing region 55 as the configuration in a front side optical sensor, the height H252 in a back side optical sensor is reduced by placing the light sensing region 55 between the wave guide region 200 and the interconnection region 73. In such arrangement, a fluorescent light from the specimen 231, such as the light 81, 82, or 83, travels a reduced distance to the light sensing region 55. By disposing the light sensing region 55 closer to the sample holding portion 23, an intensity of the fluorescent light reaches the interface S45, S534, or S523 is increased. An increased intensity results in increased quantum efficiency of the optical sensor 100. By disposing the interconnection region 73 further away from the wave guide region 200 than the light sensing region 55, electrical components such as the contact 71 or the via structure 25 are separated from optical components such as the dielectric layer 28 or the dielectric layer 27. In such displacement, the fluorescent light is traveling without the scattering and the attenuation of the metallic lines in the interconnection region 73. A signal to noise ratio of the fluorescent light can be increased by the aforesaid displacement.

The layer below the core layer 27 in FIG. 1 is the filter layer 30. In some embodiments, the filter layer 30 includes a top layer in the stacks of an alternating dielectric layers including, but not limited to, $SiO_2$ and $Ta_2O_5$. The top layer can be one of the aforesaid alternating dielectric layers with lower refractive index, for example, $SiO_2$. In some embodiments, $SiO_2$ of the alternating dielectric layer is in contact with the core layer 27. The number of repeating cycle of the alternating dielectric layers can be designed according to the target wavelength to be filtered. The layer below the core layer 27 in FIG. 3 is the dielectric layer 282. The dielectric layer 282 includes a thickness TH282 proximately around 510 nanometers, plus or minus about ten percent. In some embodiments, the thickness TH282 is substantially greater than the height H252 such that a ratio between the thicknesses TH282 of the lower cladding layer 282 and the thickness TH28 of the upper cladding layer 28 is from about 1 to about 2. In some embodiments, the dielectric layer 282 is composed of material having a refractive index smaller than the first refractive index of the core layer 27. In some embodiments, the refractive index of the dielectric layer 282 is smaller than, equal to, or greater than the second refractive index of the dielectric layer 28. Referring back to FIG. 1, the regions in the light sensing region 55 include three regions 552, 554, and 557 composed of the second conductive type dopants and two region 553 and 555 composed of the first conductive type dopants. In FIG. 3, the regions in the light sensing region 55 include two regions 552 and 554 composed of the second conductive type dopants and one region 553 composed of the first conductive type dopants. The detailed light sensing region 55 in FIG. 3 is discussed below.

An interface between a region composed of the first conductive type dopants and another region composed of the second conductive type dopants is a p-n junction. Each interface at different location, with different length, or with different orientation is capable of detecting different wavelengths of the light 81, 82, or 83 distinctively. Different combination of p-n junction serves as different photodiode capable of detecting a different wavelength of the light 81, 82, or 83. For example, an interface S45 between the region 554 and the epitaxy region 51 is a p-n junction. A first horizontal junction, such as the interface S523, is closer to the front side S1. A second horizontal junction, such as the interface S45, is closer to the back side S2.

The first horizontal junction, such as the interface S523, is closest to the front side S1. The second horizontal junction, such as the interface S45, is furthest from the front side S1 or closest to the back side S2. A distance from the first junction to the second junction is proximately from around 2 micrometers to around 3 micrometers. The first horizontal junction is smaller than the second horizontal junction. A third junction, such as the interface S534, is between the first junction and the second junction. A ratio of distances from the back side S2 to the first junction, the second junction, and the third junction respectively is in a range of from about 4:1:2 to about 9:1:3. A horizontal junction, such as the interface S45, S534, or S523, is substantially parallel to the front side S1. The horizontal junctions are parallel to each other.

Figure 4:
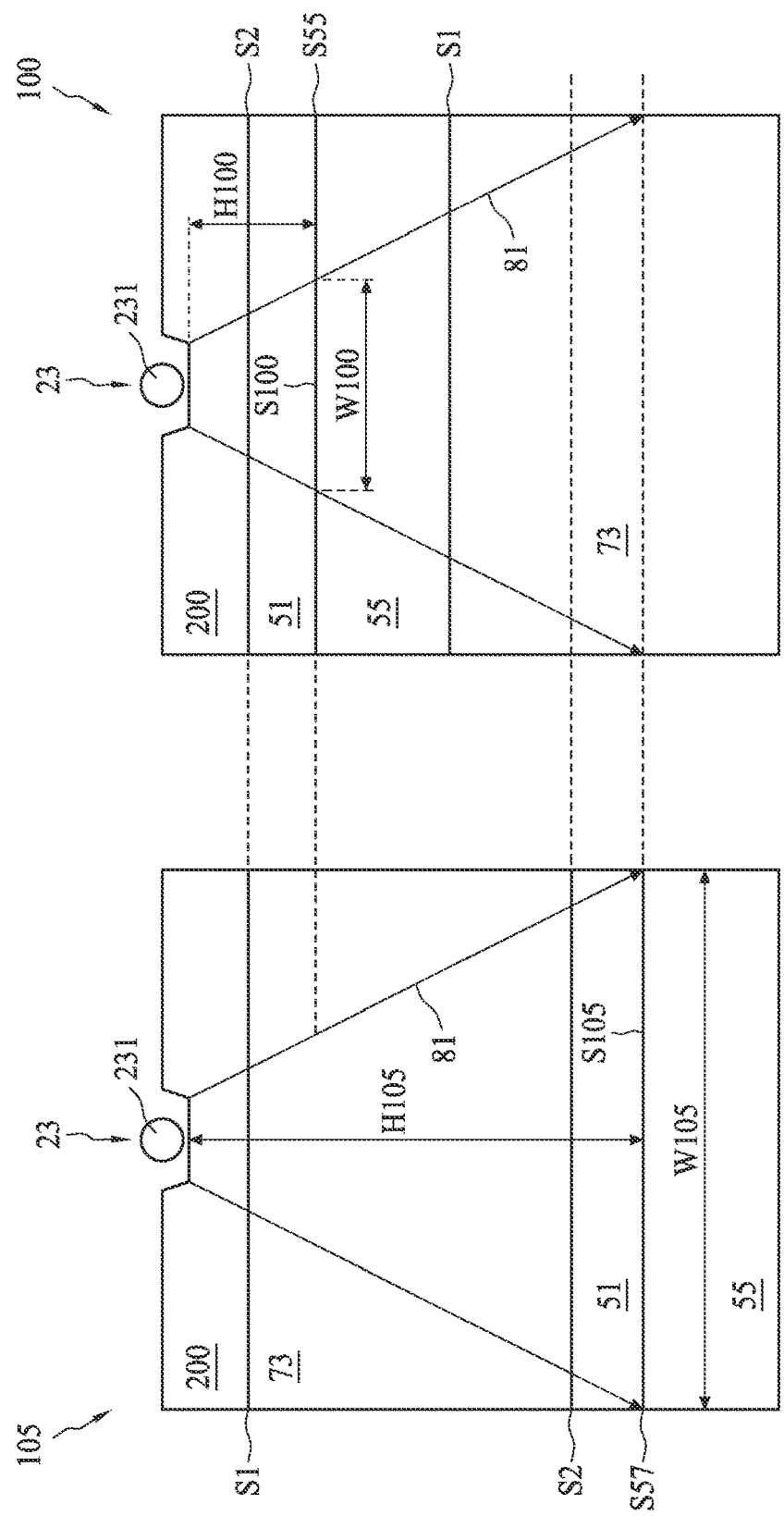

FIG. 4 illustrates a difference between some optical sensors 105 and 100. In the optical sensor 100, the light sensing region 55 is between the wave guide region 200 and the interconnection region 73. The light sensing region 55 is under the epitaxy region 51. The back side S2 is between the wave guide region 200 and the light sensing region 55. The light 81 from the sample holding portion 23 travels to a top surface S55 of the light sensing region 55. A top surface S55 includes an exposed portion S100 exposed to a certain intensity of the light 81. The exposed portion S100 includes a width W100. The certain intensity of the light 81 is inversely proportional to a square of a distance such as the height H100. The height H100 is measured in a direction orthogonal to the exposed portion S100. The height H100 is measured from a source, such as the specimen 231, to the exposed portion S100.

In the optical sensor 105, the interconnection region 73 is between the wave guide region 200 and the light sensing region 55. The back side S2 is between the interconnection region 73 and the light sensing region 55. The light 81 from the sample holding portion 23 travels to a top surface S57 of the light sensing region 55. The top surface S57 includes the exposed portion S105 exposed to the certain intensity of the light 81. The exposed portion S105 includes a width W105. The certain intensity of the light 81 is inversely proportional to a square of a distance, such as the height H105. The height H105 is measured in a direction orthogonal to the exposed portion S105. The height H105 is measured from a source, such as the specimen 231, to the exposed portion S105.

Comparing the optical sensors 105 and 100, the height H100 is smaller than the height H105. The exposed portion S100 is smaller than the exposed portion S105. The total illumination amount received by the exposed portion S100 and S105 is substantially the same since a size of the exposed portion S100 and a distance from the exposed portion S100 to the sample holding portion 23 are both reduced in the optical sensor 100. The exposed portion S100 is able to receive a certain intensity of the light 81 with a smaller size than the exposed portion S105. Reducing the distance from the specimen 231 to the exposed portion S100 by placing the light sensing region 55 between the wave guide region 200 and the interconnection region 73 allows the exposed portion S100 to be reduced. Reducing the exposed portion S100 helps to shrink a size of the light sensing region 55. In some embodiments, a pixel size of the optical sensor 100 is smaller than a pixel size of the optical sensor 105, for example, by proximately ten times.

Figure 5:
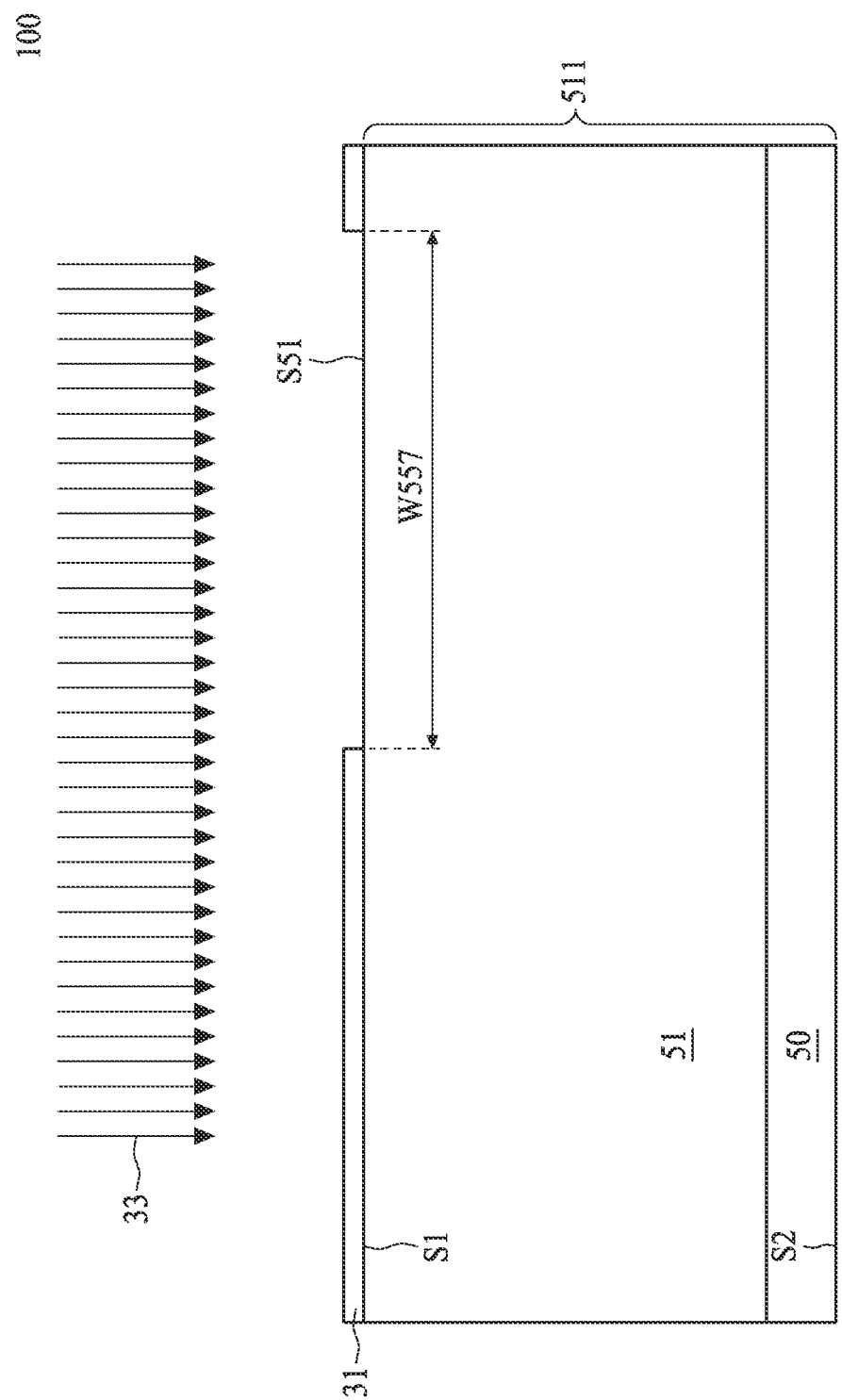
FIGS. 5-29 are cross-sectional views of an operation in a method for manufacturing an optical sensor, in accordance with some embodiments of the present disclosure.

In FIG. 5, a semiconductor material, such as silicon germanium (SiGe) or silicon (Si), is epitaxially grown above a semiconductive substrate 50 in order to form the epitaxy region 51. In an embodiment, impurities are added to the epitaxy region 51 during a growth (e.g., in-situ doping). Exemplary dopants include arsenic, phosphorous, antimony, boron, boron di-fluoride, and/or other possible impurities. Sources for boron include diborane gas used during SiGe epitaxy. Boron doped in a SiGe is accomplished by introducing boron-containing gas, in an in-situ fashion, to an epitaxial SiGe growth. In some embodiments, boron or other dopants are formed by implantation operations such that the epitaxy region 51 includes a positive dopant.

A resist 31 covers on top of a predetermined portion of the epitaxy region 51. An ion implantation operation 33 is performed over the epitaxy region 51. A resist 31 includes an opening pattern with a width W557, exposing the epitaxy region 51 to a high energy ion beam. In some embodiments, dopants of a negative type are implanted into the epitaxy region 51 through high-energy collisions at an atomic level such that the dopants are stopped below the front side S1 at a predetermined distance.

Figure 6:
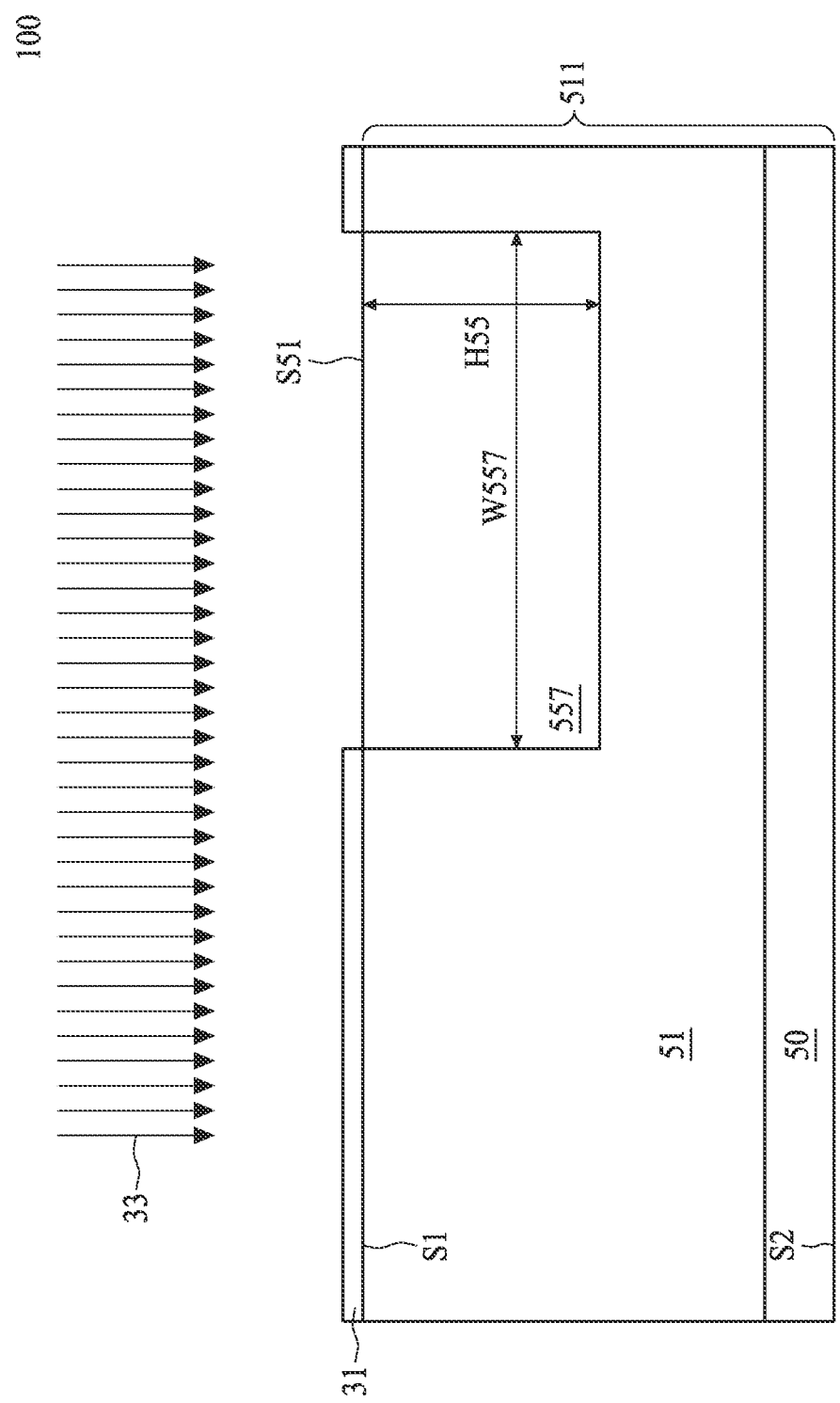

In FIG. 6, the ion implantation operation 33 implants dopants with a first predetermined energy into the epitaxy region 51 so as to form the region 557 under the front side S1 by a depth substantially equal to the height H55. The resist 31 is stripped after the region 557 is formed.

Figure 7:
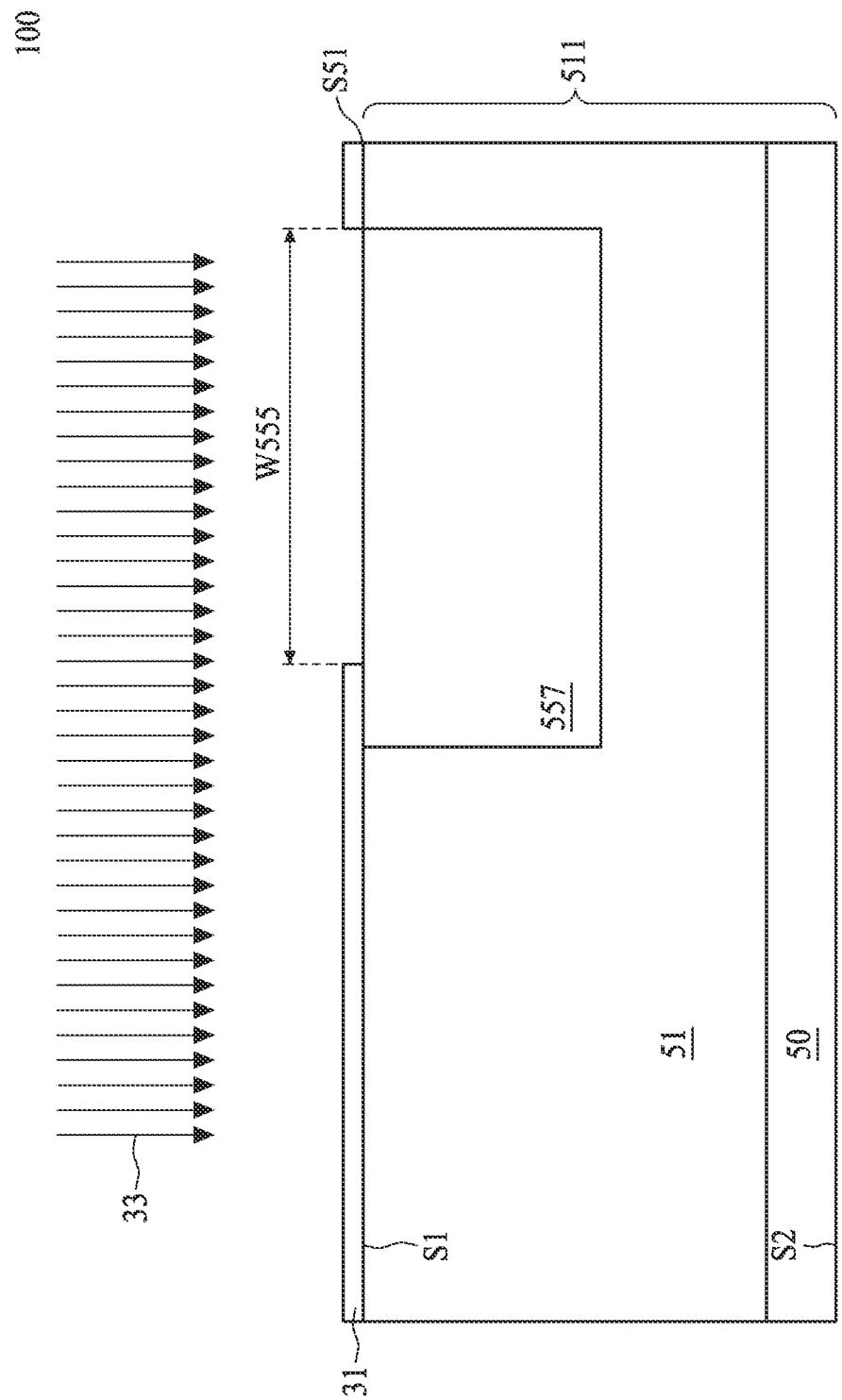

In FIG. 7, another resist 31 with an opening having a width W555 partially covers the region 557. The opening is exposing the region 557 to another ion implantation operation 33. In some embodiments, the width W555 is shorter than the width W557 for forming the region 557 shown in FIG. 6.

Figure 8:
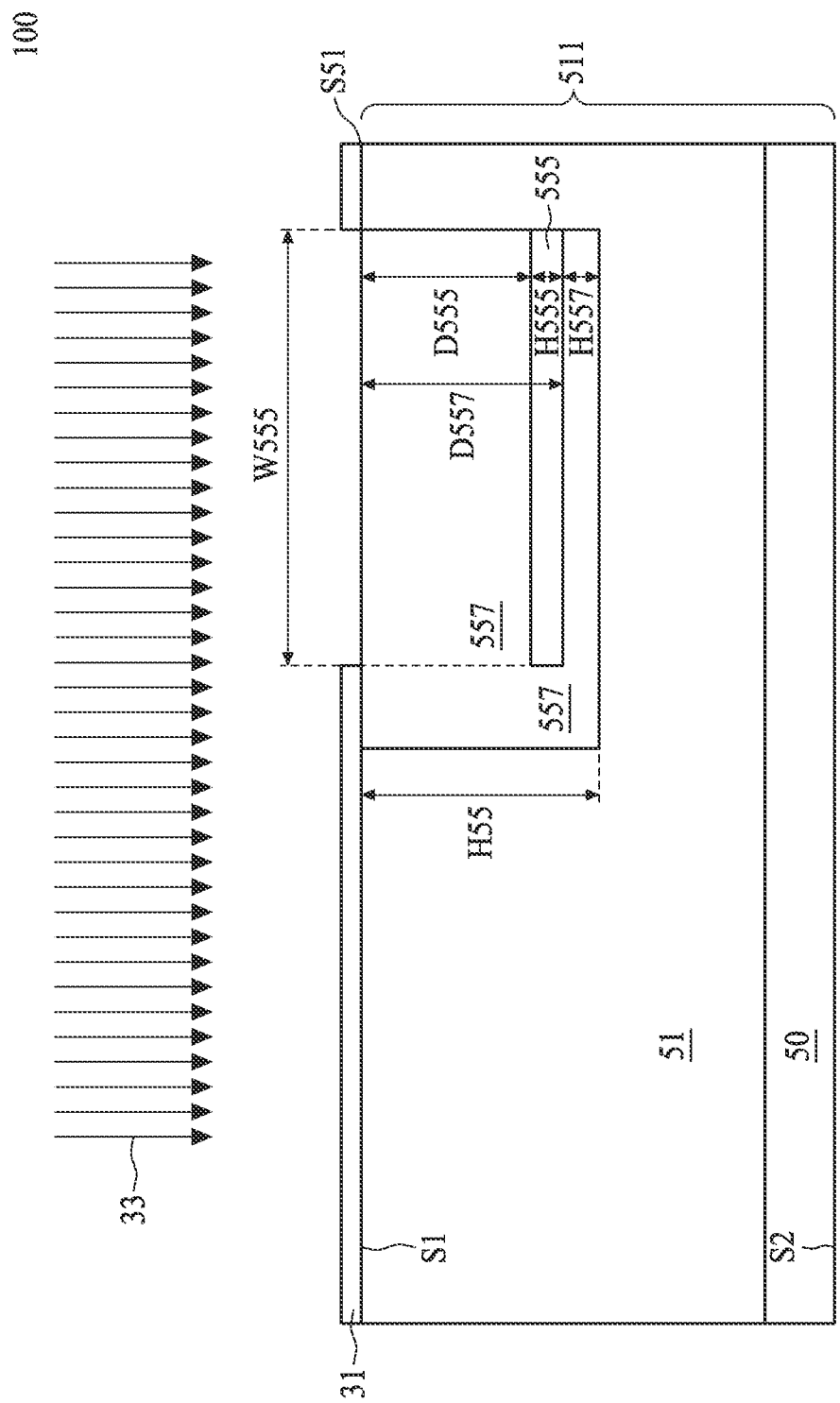

In FIG. 8, the ion implantation operation 33 implants dopants with a second predetermined energy into the region 557 so as to form a horizontal portion of the region 555 above the region 557 by a height H557 and under the front side S1 by a depth D555. The second predetermined energy is adjusted to be smaller than the first energy such that dopants are distributed around a shallower region 555 than that of the region 557. In some embodiments, the ion implantation operation 33 is performed over a front side S1 of the semiconductive block 511. In some embodiments, the dopants in the region 555 are of a same type as the epitaxy region 51, such as a positive type. The resist 31 is stripped after the region 555 is formed. The region 557 above and below the region 555 includes the dopants, such as negative dopants opposite to a conductive type of the region 555. A first semiconductor layer, such as the region 555, is formed. The first semiconductor layer is formed and includes the first conductive type.

Figure 9:
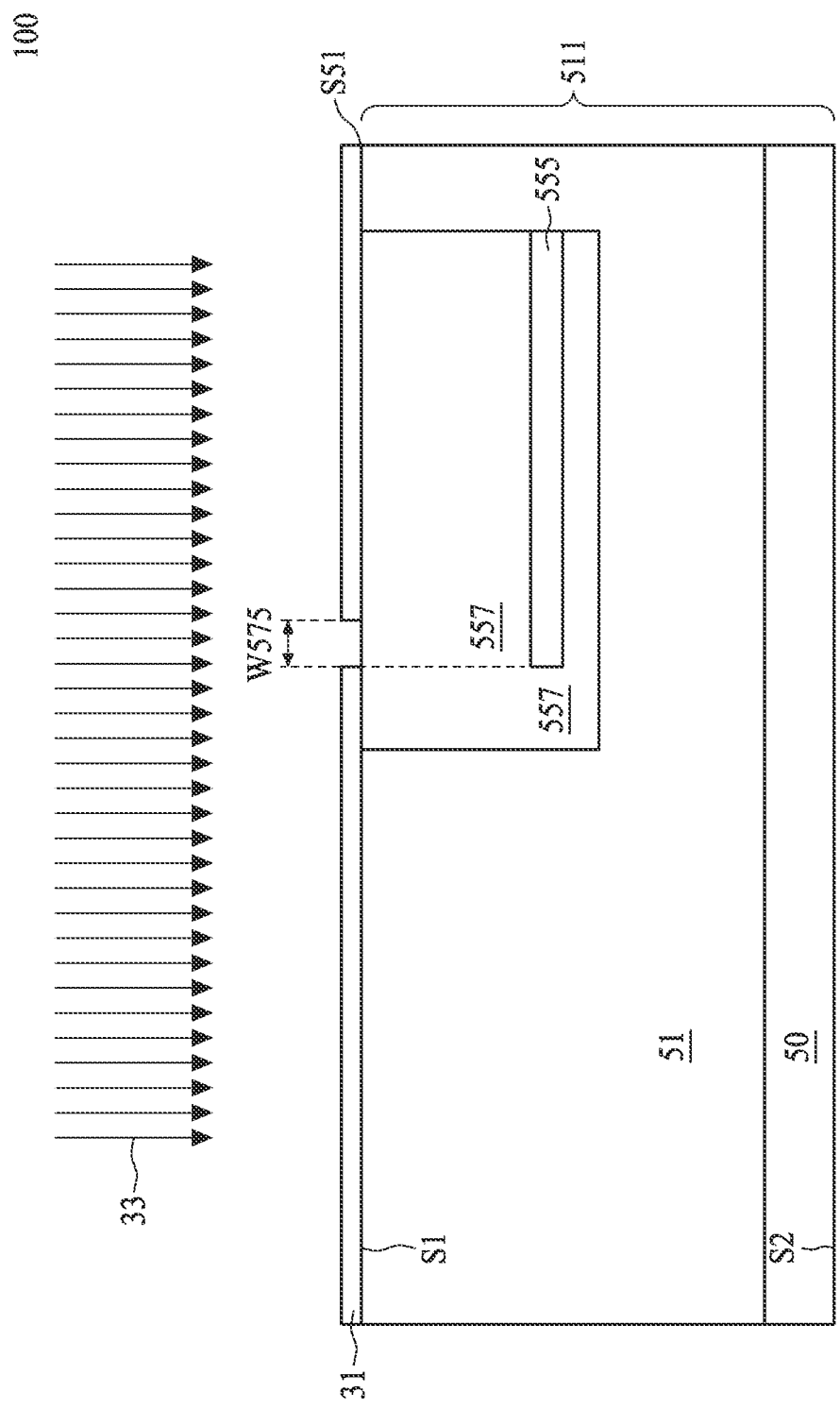

In FIG. 9, another resist 31 with an opening having a width W575 is partially covering the region 557 and the region 555 therein. The opening is exposing the region 557 to another ion implantation operation 33. The opening is aligned to one end of the region 555.

Figure 10:
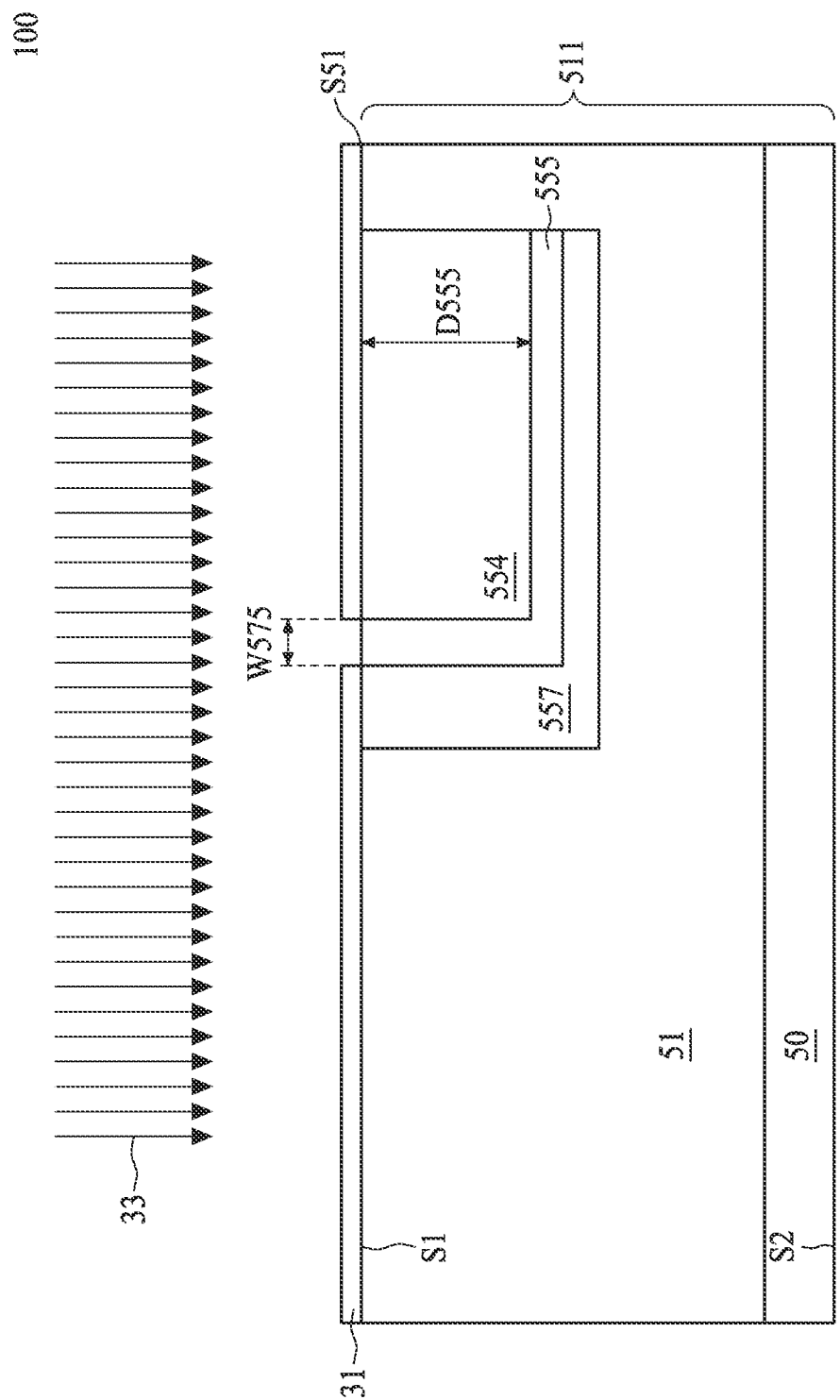

In FIG. 10, the ion implantation operation 33 implants dopants with a third predetermined energy into the region 557 so as to form a lateral portion of the region 555 above the horizontal portion of the region 555. The ion implantation 33 is performed over the front side S1 of the semiconductive block 511. The lateral portion of the region 555 includes a depth D555. The third predetermined energy is adjusted to be in a range smaller than the second energy such that dopants are implanted from the depth D555 up to the front side S1. In some embodiments, the ion implantation operation 33 conducted in FIG. 10 includes multiple operations of implantation with a variety of ion energies. In order to form a vertical implant region, different energies of ions are required to achieve said doping profile. In some embodiments, the dopants are of a same type as the horizontal portion of the region 555, such as a positive type. The resist 31 is stripped after the lateral portion of the region 555 is formed. The region 554 above the region 555 includes the dopants of an opposite conductive type to the region 555, such as negative dopants. A second semiconductor layer, such as the region 554, includes the second conductive type of dopant. The second semiconductor layer, such as the region 554, is in the first semiconductor layer, such as the region 555. In some embodiments, the second semiconductor layer is conformally formed inside the first semiconductor layer. A horizontal portion of the second semiconductor layer is closer to the front side S1 rather than a horizontal portion of the first semiconductor layer.

Figure 11:
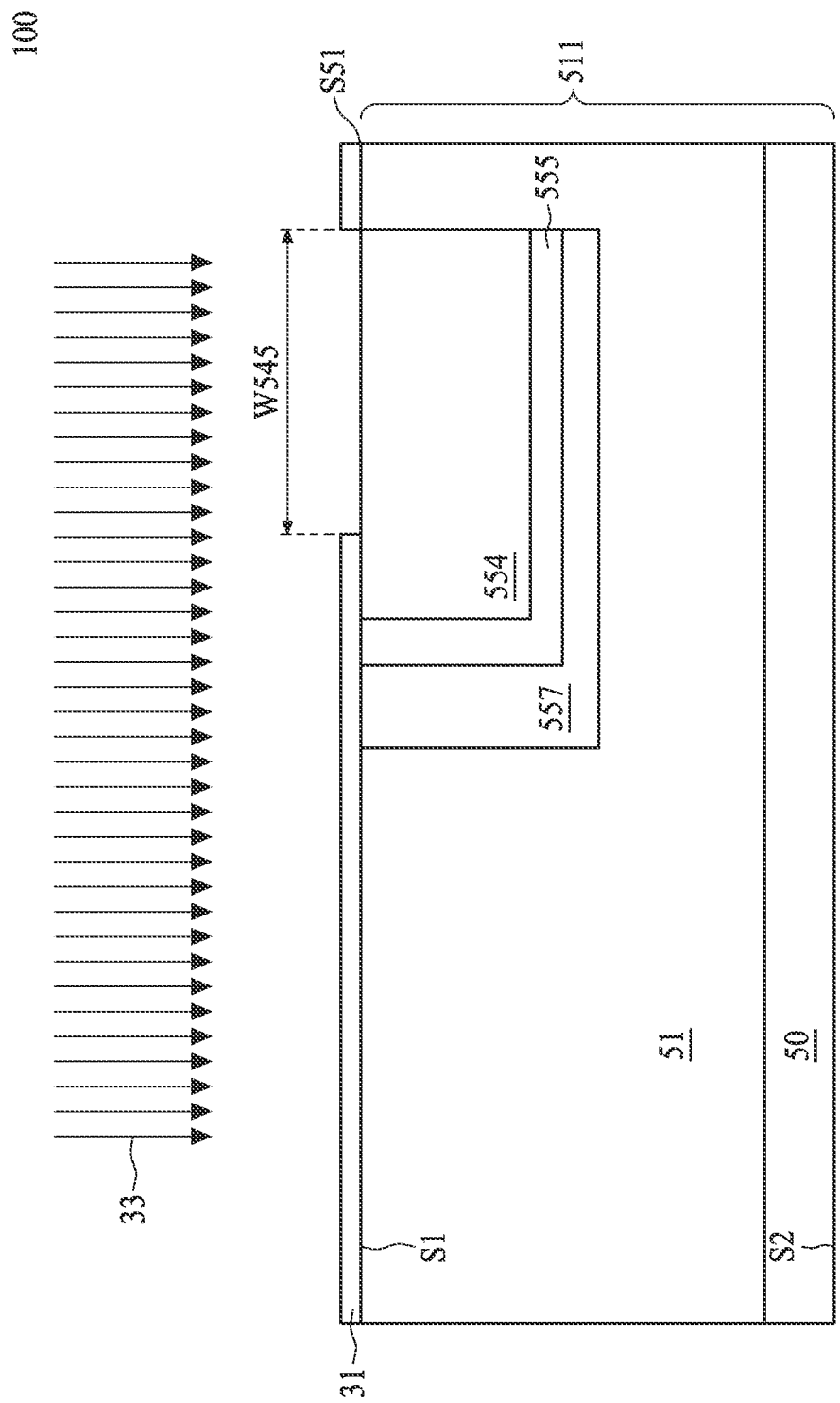

In FIG. 11, another resist 31 with an opening having a width W545 is partially covering the region 554. In some embodiments, the width W545 is shorter than the width W555 for forming the region 555 shown in FIG. 8. The opening is exposing the region 554 to another ion implantation operation 33. The opening W545 is aligned to an interface between the region 554 and the epitaxy region 51.

Figure 12:
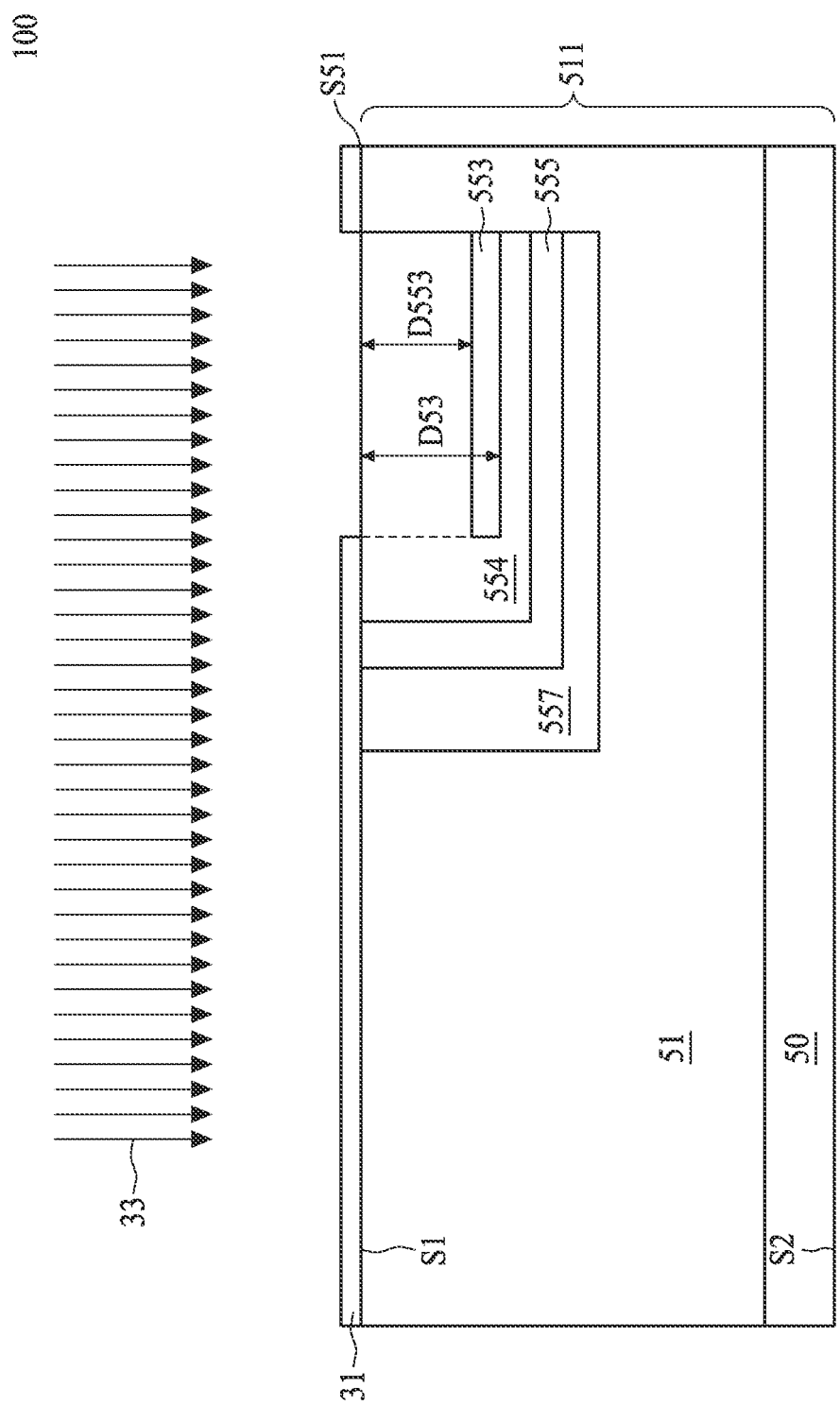

In FIG. 12, the ion implantation operation 33 implants dopants with a forth predetermined energy into the region 554 so as to form a horizontal portion of the region 553 above the horizontal portion of the region 555. The ion implantation operation 33 is performed over the front side S1 of the semiconductive block 511. The horizontal portion of the region 553 is under the front side S1 by a depth D553. The dopants are implanted from the depth D53 up to the depth D553. In some embodiments, the dopants are of a same type as the region 555, such as a positive type. The resist 31 is stripped after the horizontal portion of the region 553 is formed. The region 554 above the region 555 includes the dopants of an opposite conductive type to the region 553, such as negative dopants.

Figure 13:
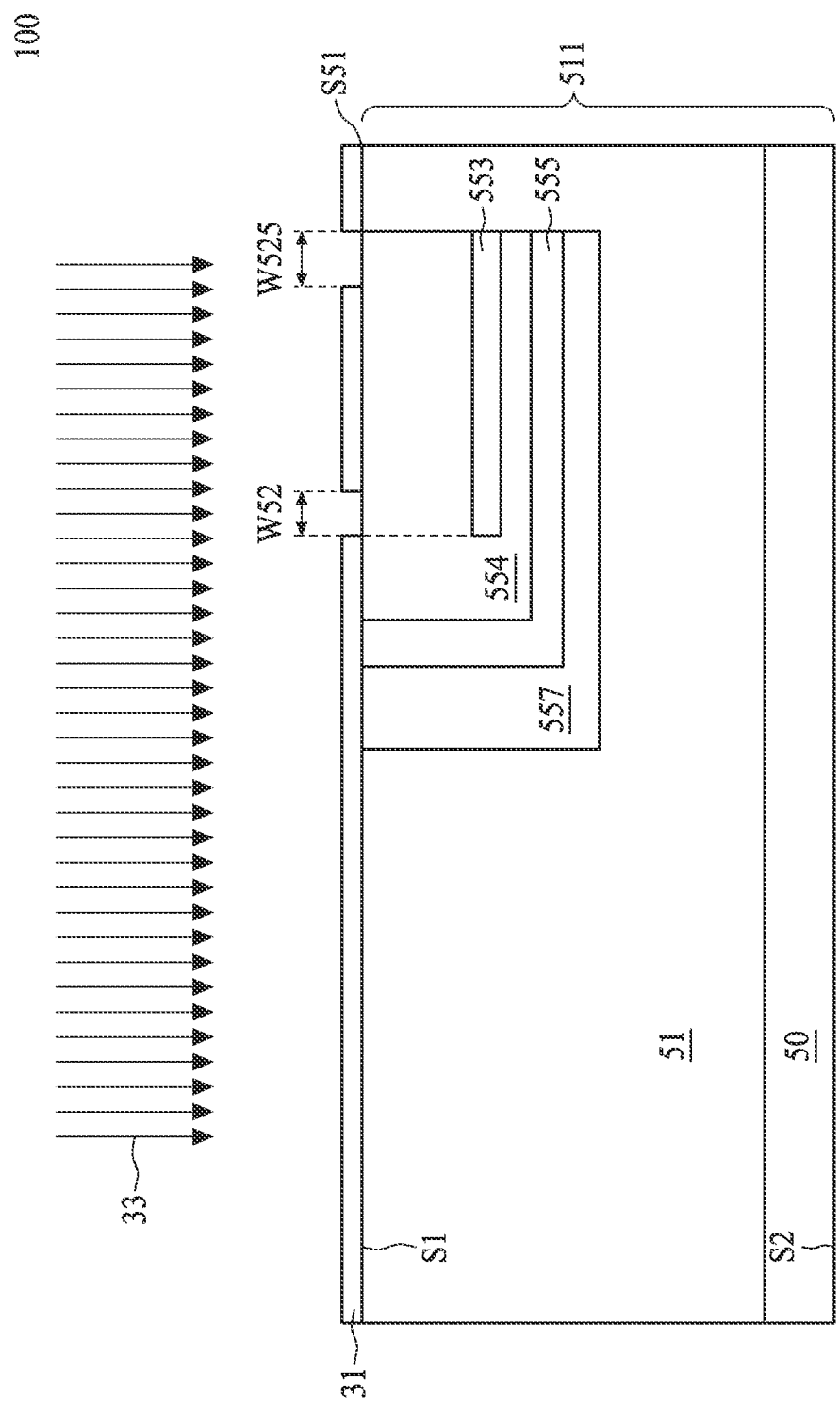

In FIG. 13, another resist 31 with a first opening having a width W525 and a second opening having a width W52 is partially covering the region 554 over the horizontal portion of the region 553. The first and the second openings are exposing the underlying region 554 to another ion implantation operation 33. The second opening is aligned to an end of the region 553. The first opening is aligned to an interface between the region 553 and the epitaxy region 51.

Figure 14:
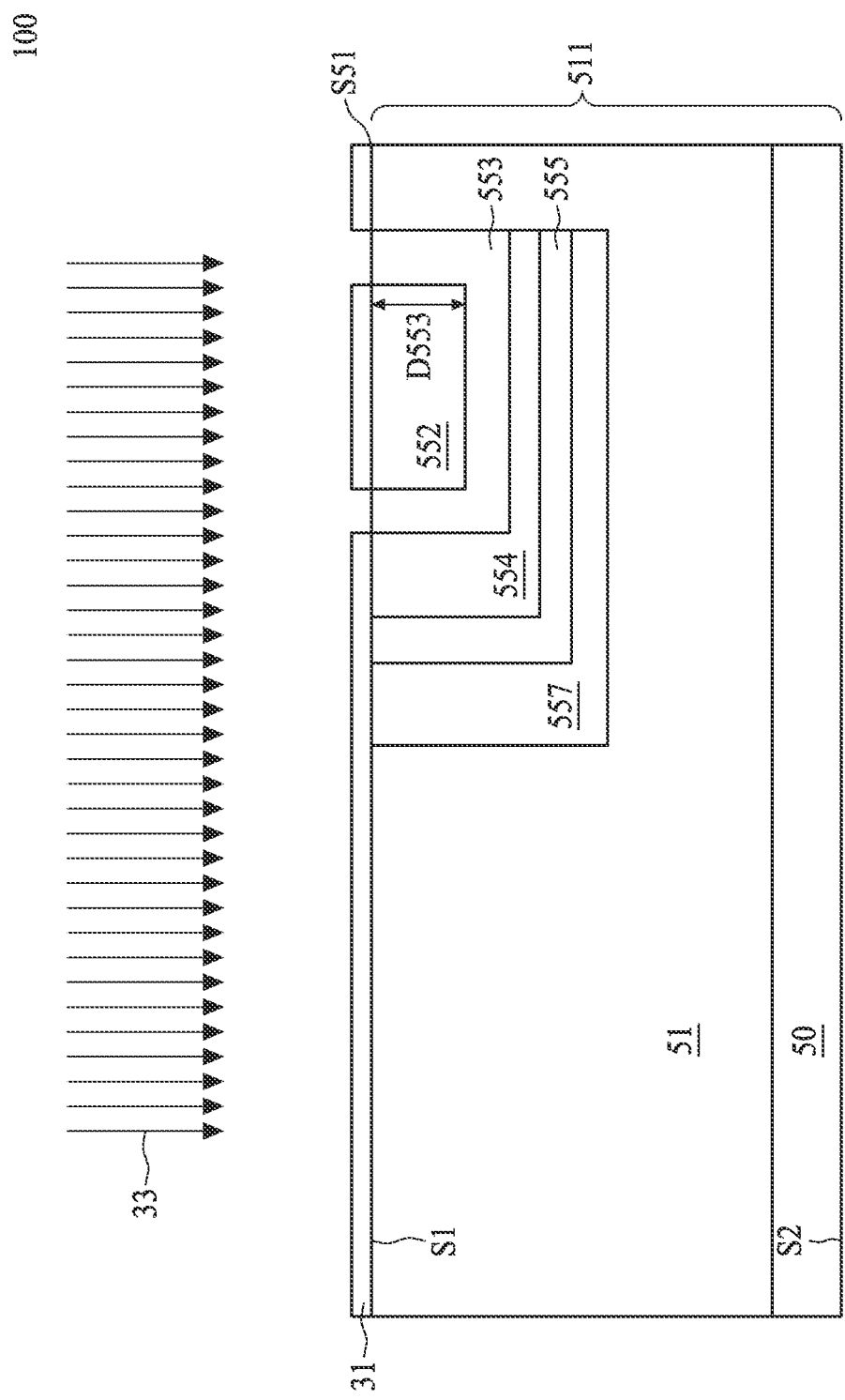

In FIG. 14, the ion implantation operation 33 implants dopants with a fifth predetermined energy into the region 554 so as to form a lateral portion of the region 553 above the horizontal portion of the region 553. The lateral portion of the region 553 includes the depth D553. The dopants are implanted from the depth D553 up to the front side S1. In some embodiments, the ion implantation operation 33 in FIG. 14 includes multiple operations of implantation with a variety of ion energies. In some embodiments, the dopants are of a same type as the region 555, such as a positive type. The resist 31 is stripped after the lateral portion of the region 555 is formed. The region 552 partially surrounded by the region 553 includes the dopants of an opposite conductive type to the region 553, such as negative dopants.

Figure 15:
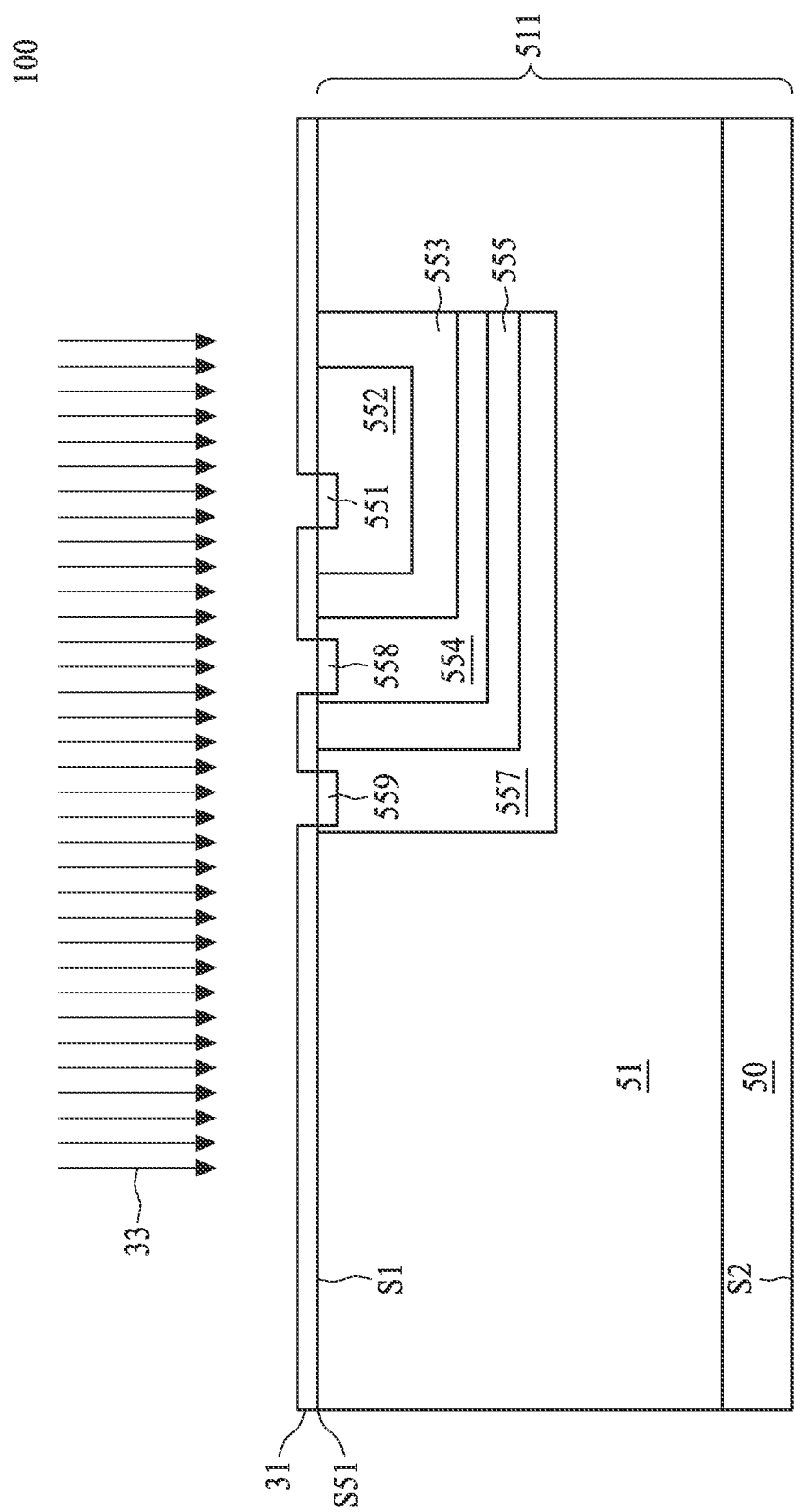

In FIG. 15, contact plugs 551, 558, and 559 are formed as highly doped regions in the semiconductor layers, such as regions 552, 554, and 557 respectively. The highly doped regions are in contact with the front side S1. In FIG. 15, another resist 31 with three openings is partially covering regions 552, 554, and 557. The three openings are exposing portions of underlying regions 552, 554, and 557 to another ion implantation operation 33.

The ion implantation operation 33 implants dopants into regions 552, 554, and 557 to form contact plugs 551, 558, and 559. In some embodiments, the dopants are of a same type as the region 557, 555, or 552, such as a negative type. The dopant concentration is substantially greater than that in the regions 552, 554, and 557. The resist 31 is stripped after the contact plugs 551, 558, and 559 are formed.

Figure 16:
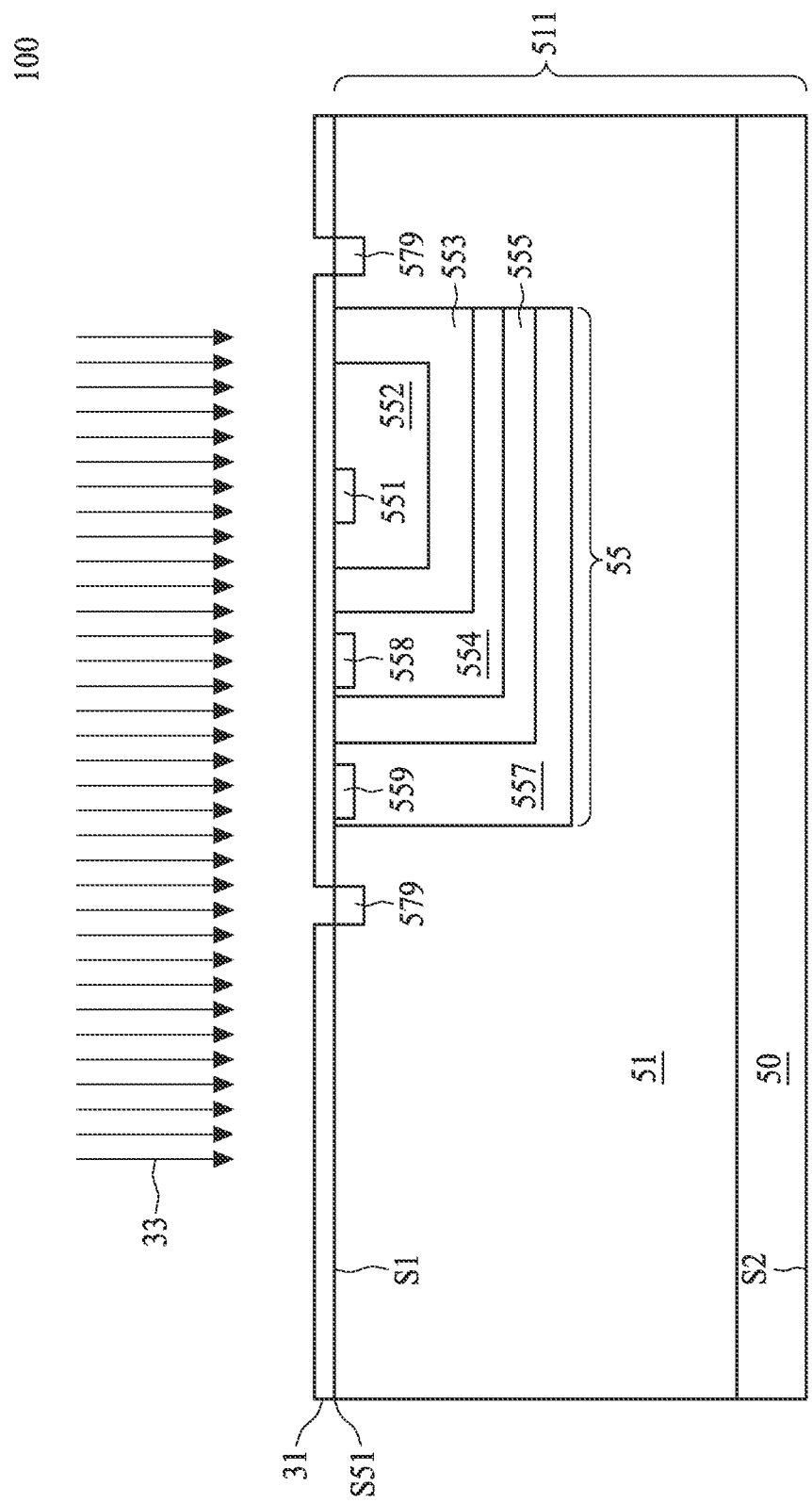

In FIG. 16, in some other embodiments, highly-doped regions 579 are formed by a patterning resist 31 with openings in the epitaxy region 51 outside of the light sensing region 55. In some other embodiments, highly-doped regions 579 are formed such that a depth or doping concentration of the highly-doped regions 579 is different from that of the region 552, 554, or 557.

In FIG. 17, another highly-doped region 578 is formed by a similar operation as that for forming the highly-doped region 579. In some embodiments, energy used in ion implantation for forming the highly-doped region 578 is higher than that for forming the highly-doped region 579 such that the highly-doped region 578 is formed deeper into the epitaxy region 51. In some embodiments, the highly-doped region 578 is formed with a higher doping concentration than the highly-doped region 579 or the light sensing region 55. The highly-doped region 578 or 579 is formed surrounding a periphery of the light sensing region 55 so as to avoid noise impact from outer circuits and cross-talk from adjacent photodiodes (not shown). In some embodiments, the highly-doped region 578 includes an opposite conductive type than that of the highly-doped region 579. For example, the highly-doped region 579 includes the first conductive type of positive dopants. The highly-doped region 578 includes the second conductive type of negative dopants. The highly-doped region 578 or 579 prevents negative or positive charge carriers from reaching the light sensing region 55. The highly-doped regions 578 and 579 are separated from each other.

Figure 18:
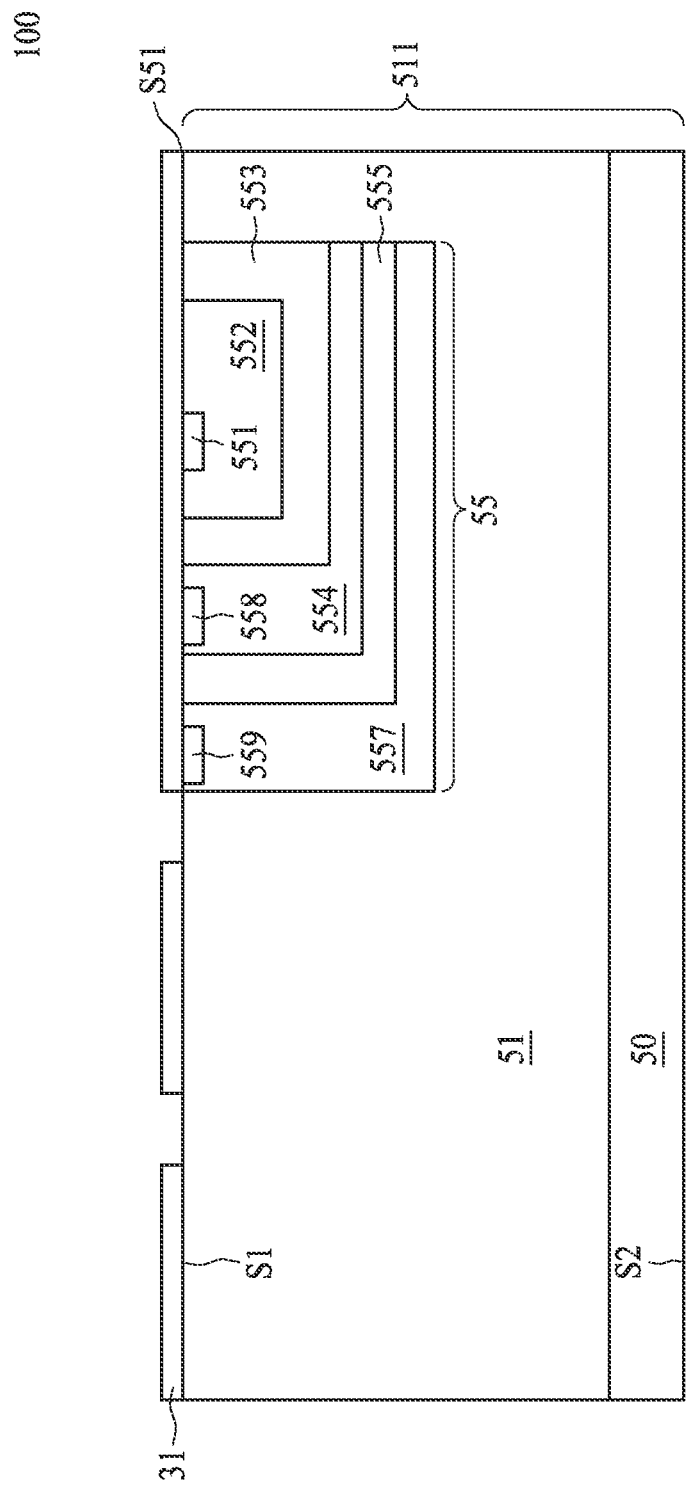

FIG. 18 is an operation following that within FIG. 15. In FIG. 18, a resist 31, including a pattern for forming isolations, is covered over the front side S1.

Figure 19:
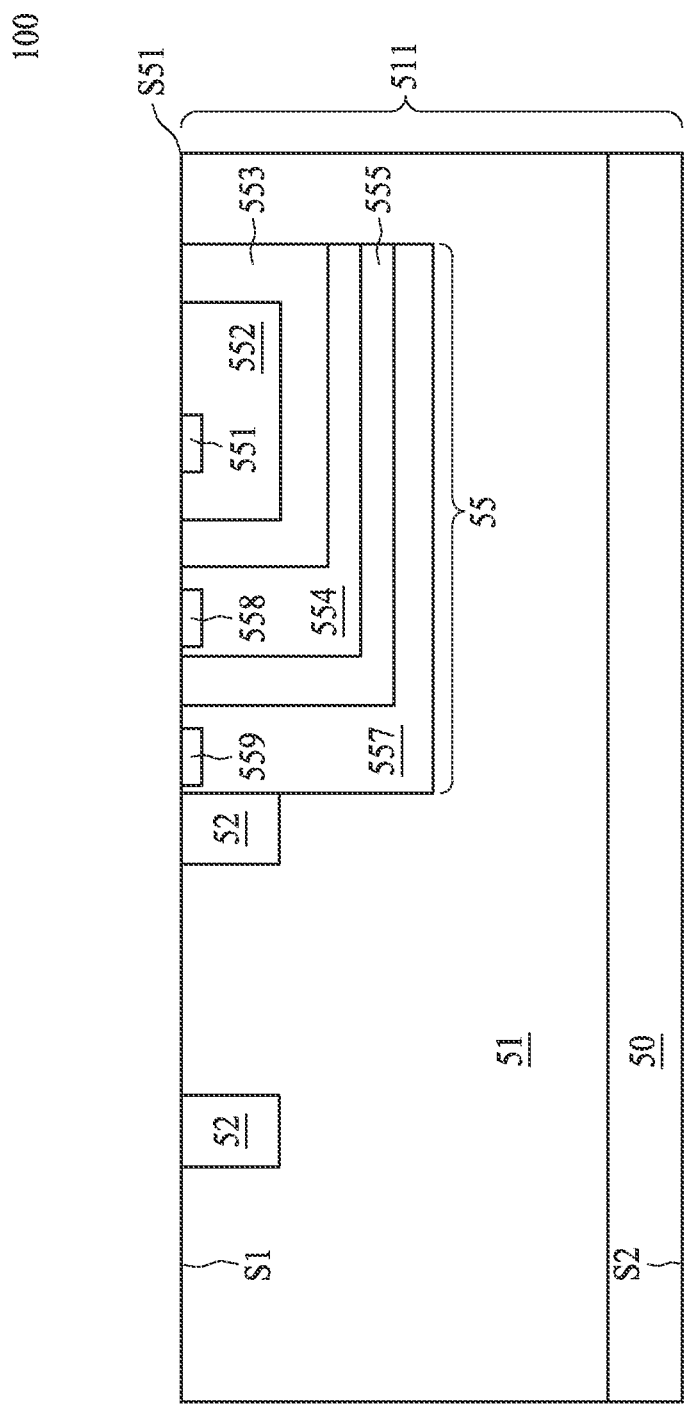

In FIG. 19, the epitaxy region 51 includes the isolation region 52 formed by etching a trench in the epitaxy region 51 on the front side S1 and filling the trench with insulator materials, such as silicon oxide, silicon nitride, or silicon oxynitride.

Figure 20:
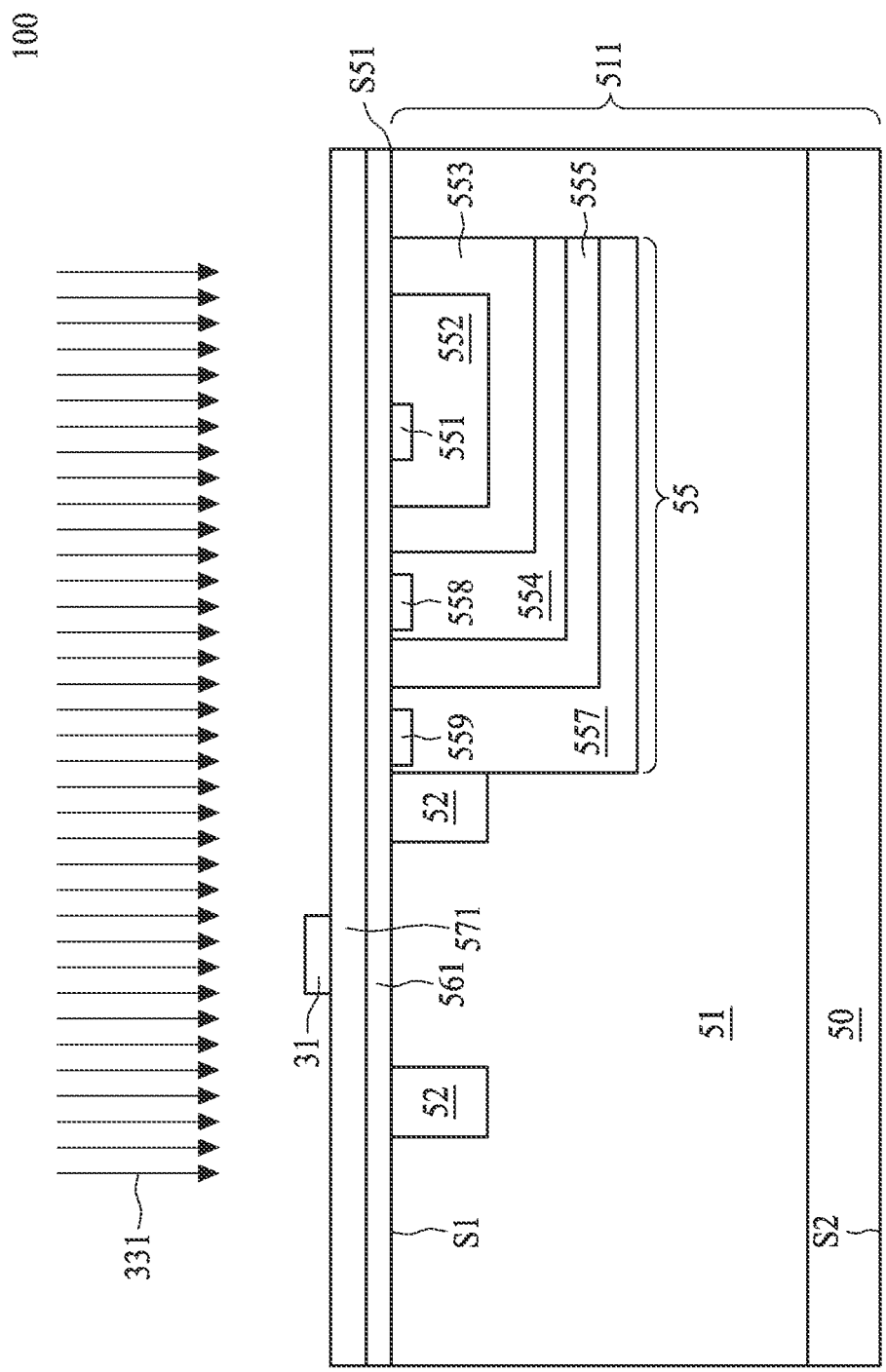

In FIG. 20, a gate dielectric layer 561 covers over the front side S1. In an embodiment, the gate dielectric layer 561 is a thin film formed by a suitable deposition process. A gate electrode layer 571 covers on top of the gate dielectric layer 561. In an embodiment, the gate dielectric layer 561 and the gate electrode layer 571 are sequentially deposited over the front side S1 by some deposition processes. In some embodiments, the gate dielectric layer 561 and the gate electrode layer 571 are only deposited over a predefined region for forming transistor structures. The gate electrode layer 571 is made of any suitable material, such as polysilicon. The gate dielectric layer 561 and the gate electrode layer 571 are patterned by a lithographic process.

Figure 21:
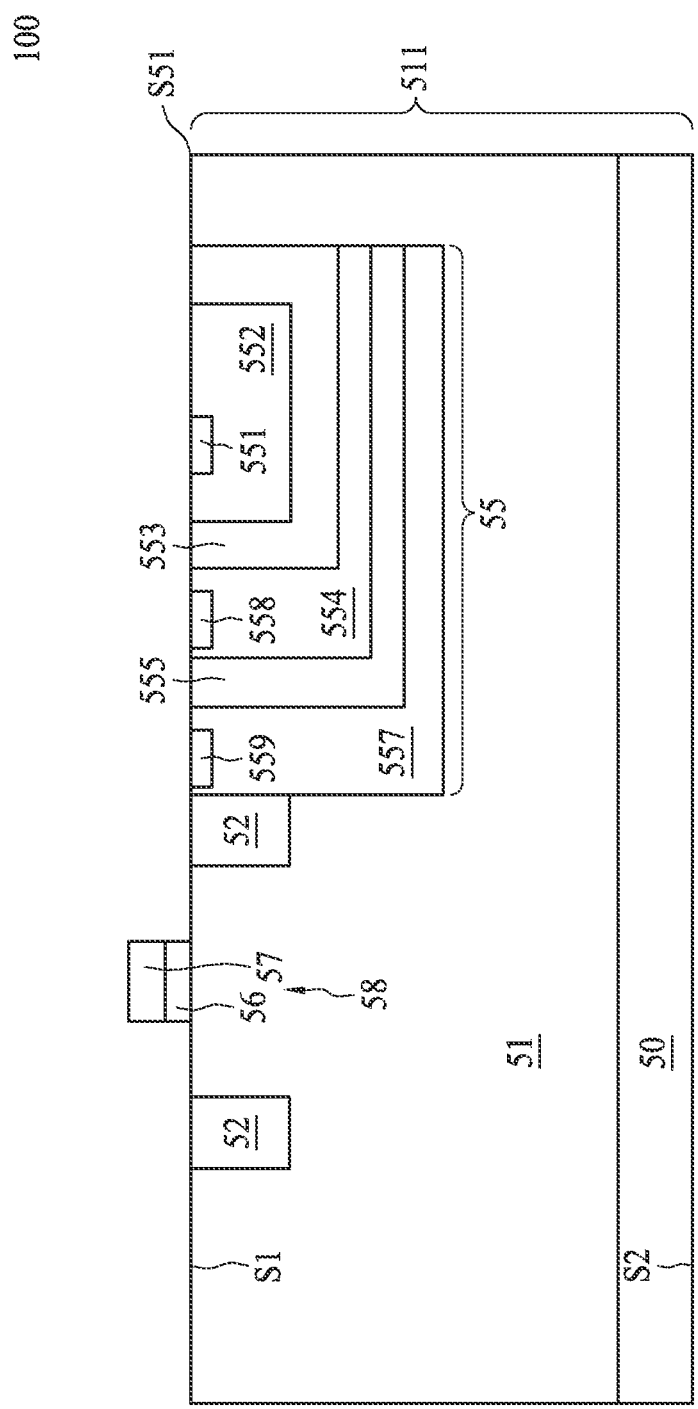

In FIG. 21, the resist feature is transferred to form a gate structure 58 on the front side S1 and in between the isolation regions 52. The gate structure 58 includes a gate electrode 57 and a gate dielectric 56.

Figure 22:
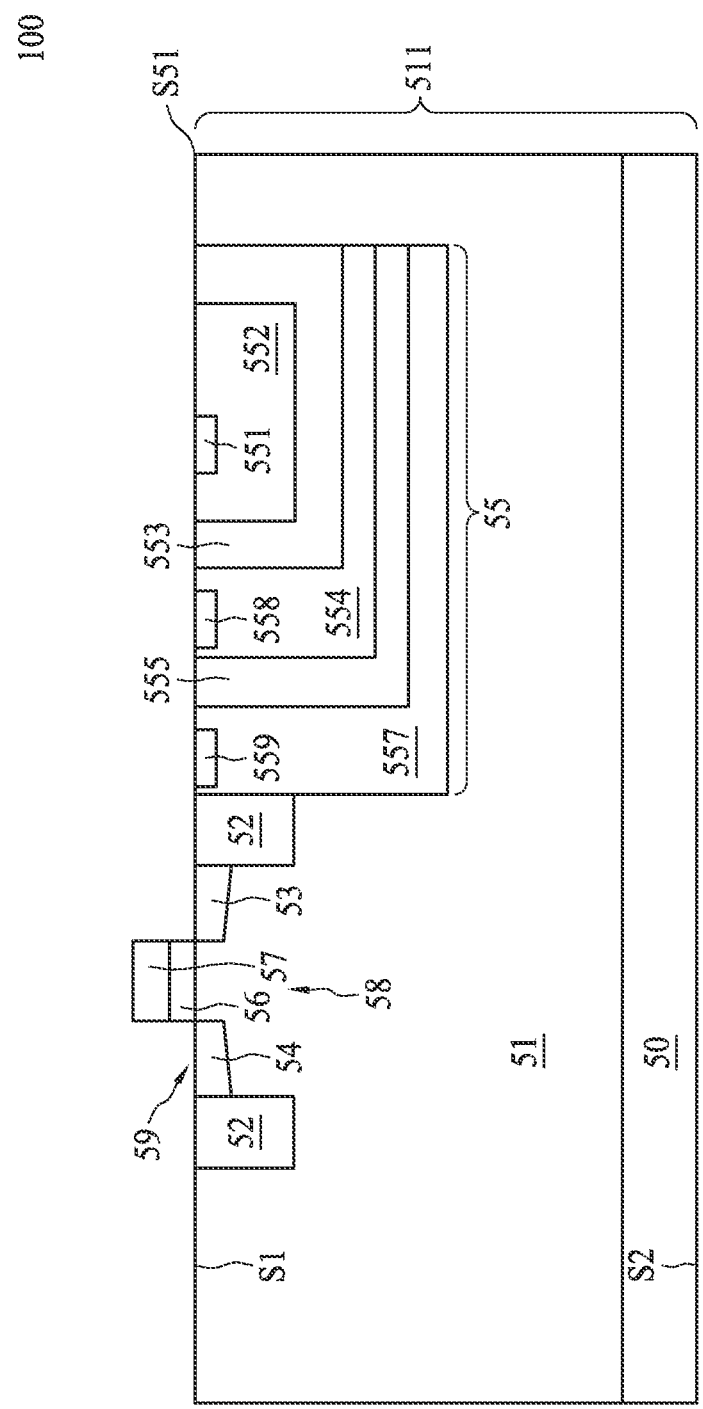

In FIG. 22, in some embodiments, a source region 53 or a drain region 54 is formed by ion implantation or epitaxial growth. The ion implantation or epitaxial growth introduces dopants in the source region 53 or the drain region 54. In various embodiments, the source region 53 or the drain region 54 has different doping profiles formed by a multi-process implantation.

Figure 23:
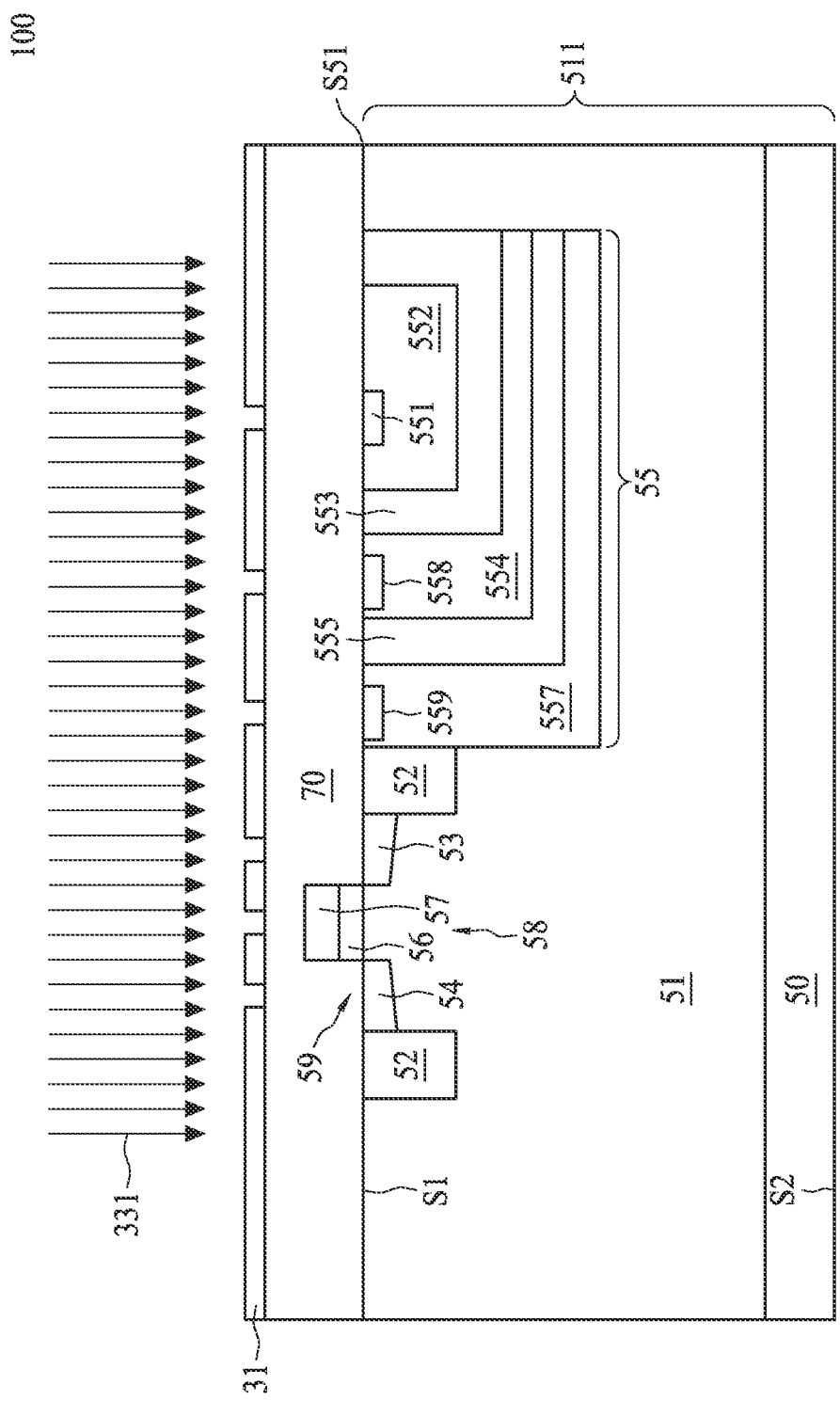

In FIG. 23, the dielectric layer 70 covers over the front side S1 by any suitable process, such as the deposition process. The dielectric layer 70 is in contact with the gate structure 58. A resist 31 is formed on top of the dielectric layer 70. Etching operations 331 are performed to transfer a patterned resist feature to the dielectric layer 70.

Figure 24:
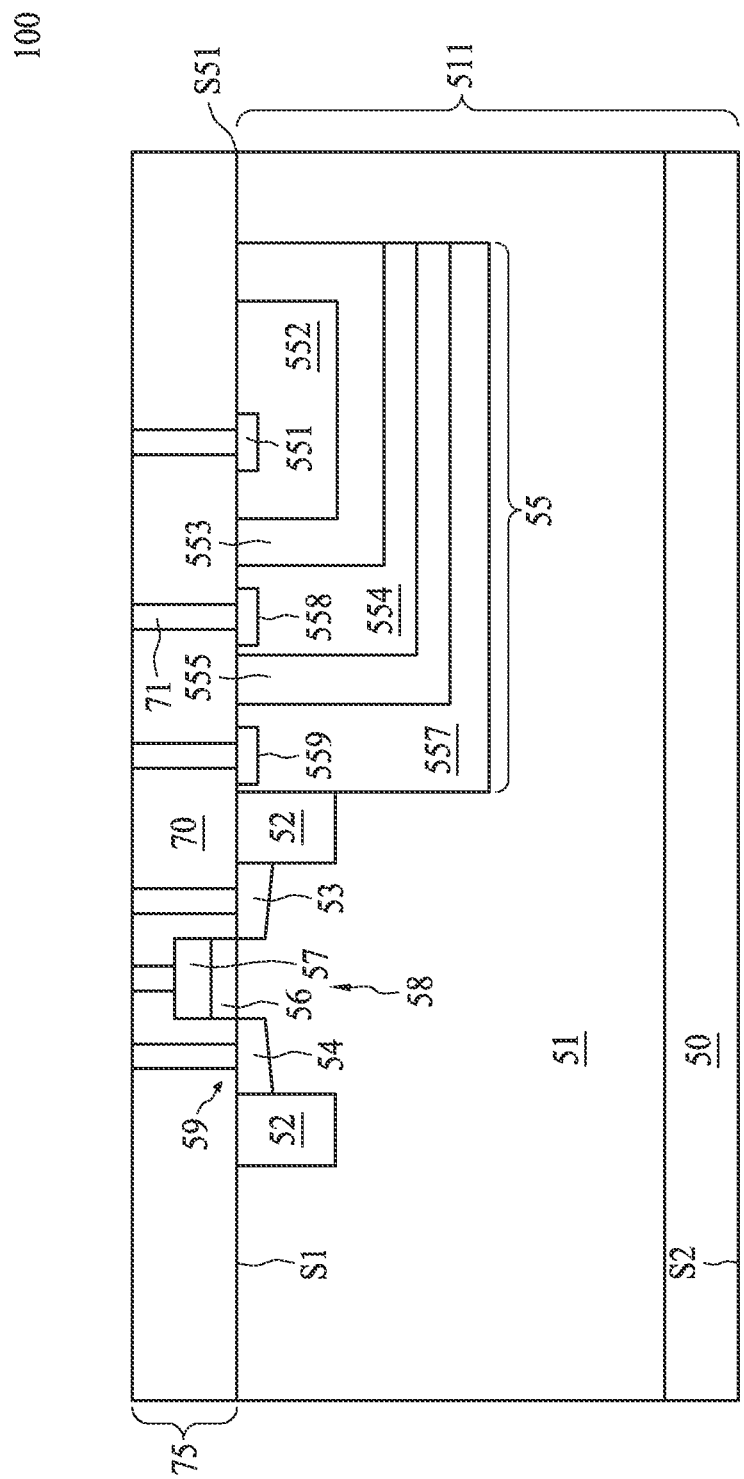

In FIG. 24, the patterned resist feature is transferred to the dielectric layer 70 so as to form trenches. In some embodiments, the trenches are formed by any suitable etching process, such as selective etching, dry etching, and/or combinations thereof. The trenches are filled by conductive materials so as to form contacts 71. The contacts 71 are formed by filling the trenches by suitable processes, such as a deposition process. The contacts 71 are electrically coupled with the gate structure 58, the source region 53, the drain region 54, the contact plug 559, the contact plug 558, and the contact plug 551. A depth of the contacts 71 is controlled by adjusting process parameters in a CVD process. The process parameters include a total pressure, reactant concentrations, deposition temperature, or a deposition rate.

Figure 25:
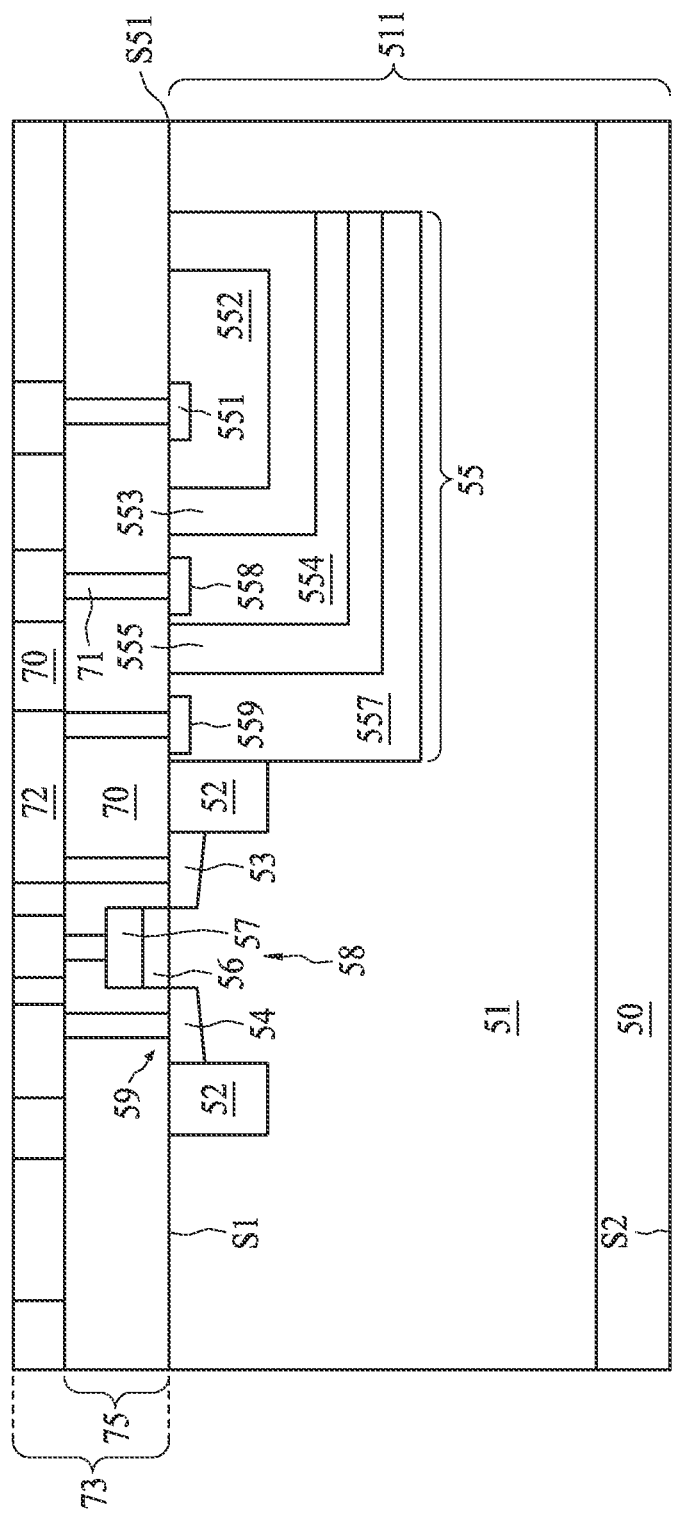

In FIG. 25, a conductive layer is deposited and patterned by transferring a resist feature to the conductive layer. The resist feature is transferred to the conductive layer so as to form recesses and interconnects 72. The recesses are filled by dielectric materials so as to form another dielectric layer 70 over the ILD layer 75. The interconnects 72 are between the dielectric layer 70. The interconnection region 73 is formed at a first side, such as the front side S1 of the semiconductive block 511. The interconnection region 73 includes the ILD layer 75, the dielectric layer 70, and the interconnects 72. In FIG. 25, multiple layers of interconnects 72 and dielectric layers 70 are deposited and etched so as to form an interconnection region 73. In some embodiments, via structures 25 are formed so as to couple metal lines in different layers.

Figure 26:
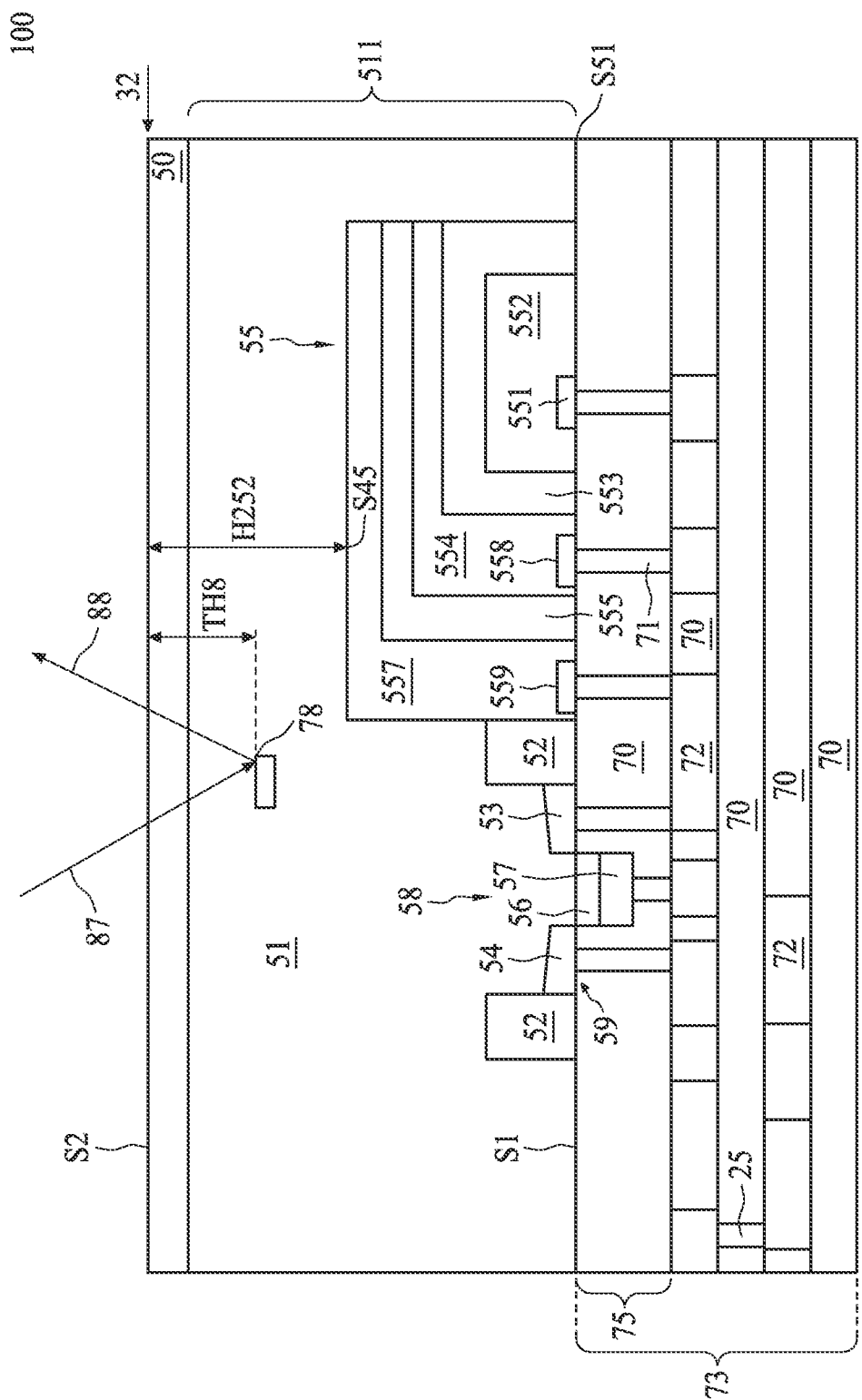

In FIG. 26, a semiconductive device such as the optical sensor 100 is flipped upside down such that a second side, such as the back side S2, is disposed above the first side as shown in FIG. 26. In some embodiments, the semiconductive substrate 50 is planarized by a planarization operation 32. The planarization operation 32 is any suitable operation, such as etching back or chemical mechanical polishing (CMP). The planarization operation 32 is performed such that the semiconductive substrate 50 disposed above the epitaxy region 51 is thinned down. In some embodiments, the semiconductive substrate 50 is thinned down to an extent that the epitaxy region 51 in proximity to the back side S2 is exposed (not shown in FIG. 26). In the aforesaid embodiment, the overlying optical stacks such as the filter layer 30 and the dielectric layer (27, 28) are disposed directly on the epitaxy region 51. In other embodiments, the semiconductive substrate 50 is partially thinned down to an extent that the epitaxy region 51 in proximity to the back side S2 is not exposed. In the aforesaid embodiments, the overlying optical stacks such as the filter layer 30 and the dielectric layer (27, 28) are disposed directly on the semiconductive substrate 50. In still another embodiment, the semiconductive substrate 50 is retained as is without any thinning operation.

The planarization operation 32 is performed such that the height H252 from the back side S2 to the interface S45 is reduced. In some embodiments, endpoint detection is used to reduce the height H252 by a predetermined amount. For example, as the back side S2 is thinned down by the planarization operation 32, a light 87 can be used for endpoint detection. In some embodiments, the light 87 is a monochromatic light source which is reflected from a surface of the back side S2. A reflected light 88 reflects from an interface 78 below the back side S2 or above the interface S45. The interface 78 is formed by some inserted dielectric layer or reflective layer in the epitaxy region 51. As the planarization operation 32 exposes the interface 78, an optical property of the reflected light 88 changes so as to indicate that an endpoint is reached, or will be reached by a predetermined distance.

In some other embodiments, endpoint detection is by measuring a resistance of some embedded wires (not shown) in the semiconductive block 511. As the planarization operation 32 reduces the thickness TH8 and any of a dimension, for example, a thickness or a length, of the embedded wire, the resistance is changed accordingly. The planarization operation 32 stops at a predetermined resistance of the embedded wire. In some embodiments, the embedded wire is connected from the front side S1 to the back side S2.

Figure 27:
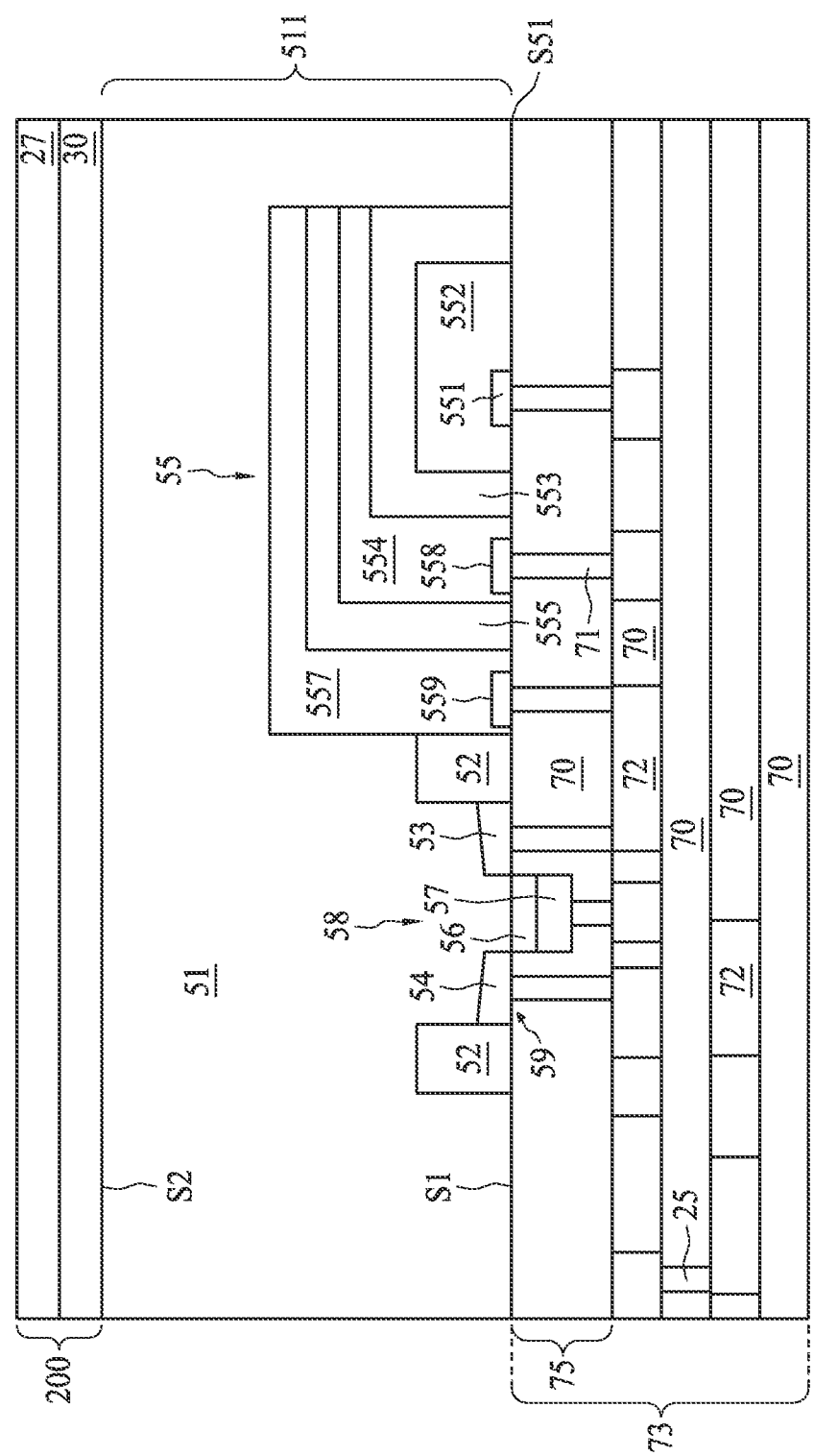

In FIG. 27, the wave guide region 200 is formed at the second side, such as the back side S2 opposite to the first side S1 of the semiconductive block 511. The filter layer 30 is blanket formed over the interconnection region 73 by any suitable process, such as deposition. In FIG. 27, the dielectric layer 27 is blanket formed on top of the filter layer 30.

In FIG. 27, the dielectric layer 27 is formed by the suitable deposition process. The dielectric layer 27 is composed of material with the first refractive index higher than the second refractive index of the dielectric layer 28.

In some other embodiments, a first cladding layer (not shown) is formed on top of the filter layer 30. A core layer, such as the dielectric layer 27, is subsequently formed on top of the first cladding layer. A second cladding layer, such as the dielectric layer 28, is subsequently blanket formed over the dielectric layer 27 as shown in FIG. 28.

Figure 28:
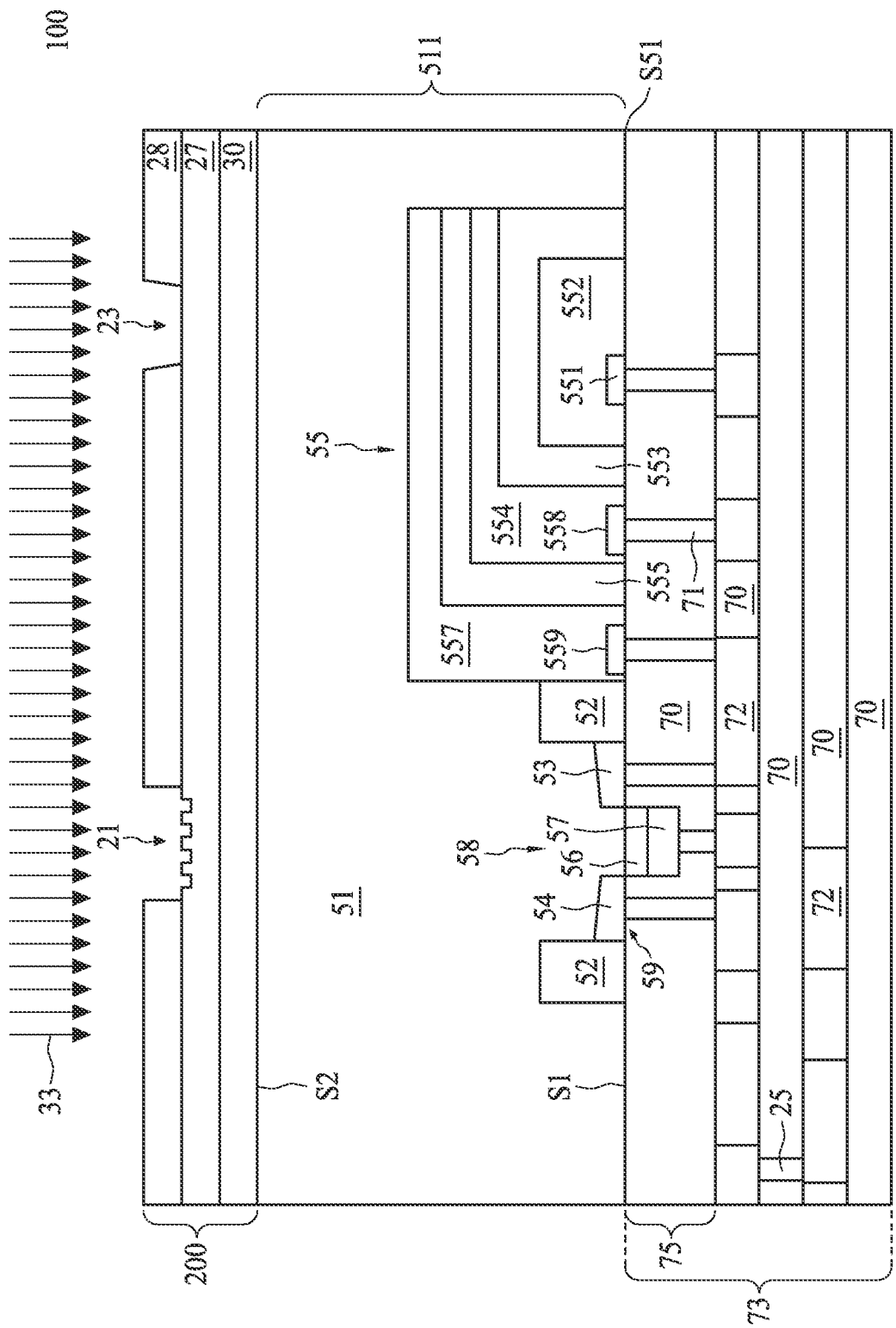

In FIG. 28, the dielectric layer 28 above the dielectric layer 27 is patterned with a recess of the sample holding portion 23 by any suitable method, such as the etching operations 33 in the lithographic operation. In some embodiments, the etching operation 33 is a selective etching.

In some embodiments, the dielectric layer 28 is deposited on the dielectric layer 27. Then the dielectric layer 28 is patterned to form an opening above the dielectric layer 27. The grating structure 21 is formed under the opening and in the dielectric layer 27 by any suitable patterning process.

In some embodiments, the dielectric layer 28 can be formed as an upper cladding layer 28 patterned by the etching operation to form the sample holding portion 23 such as a nanowell.

Figure 29:
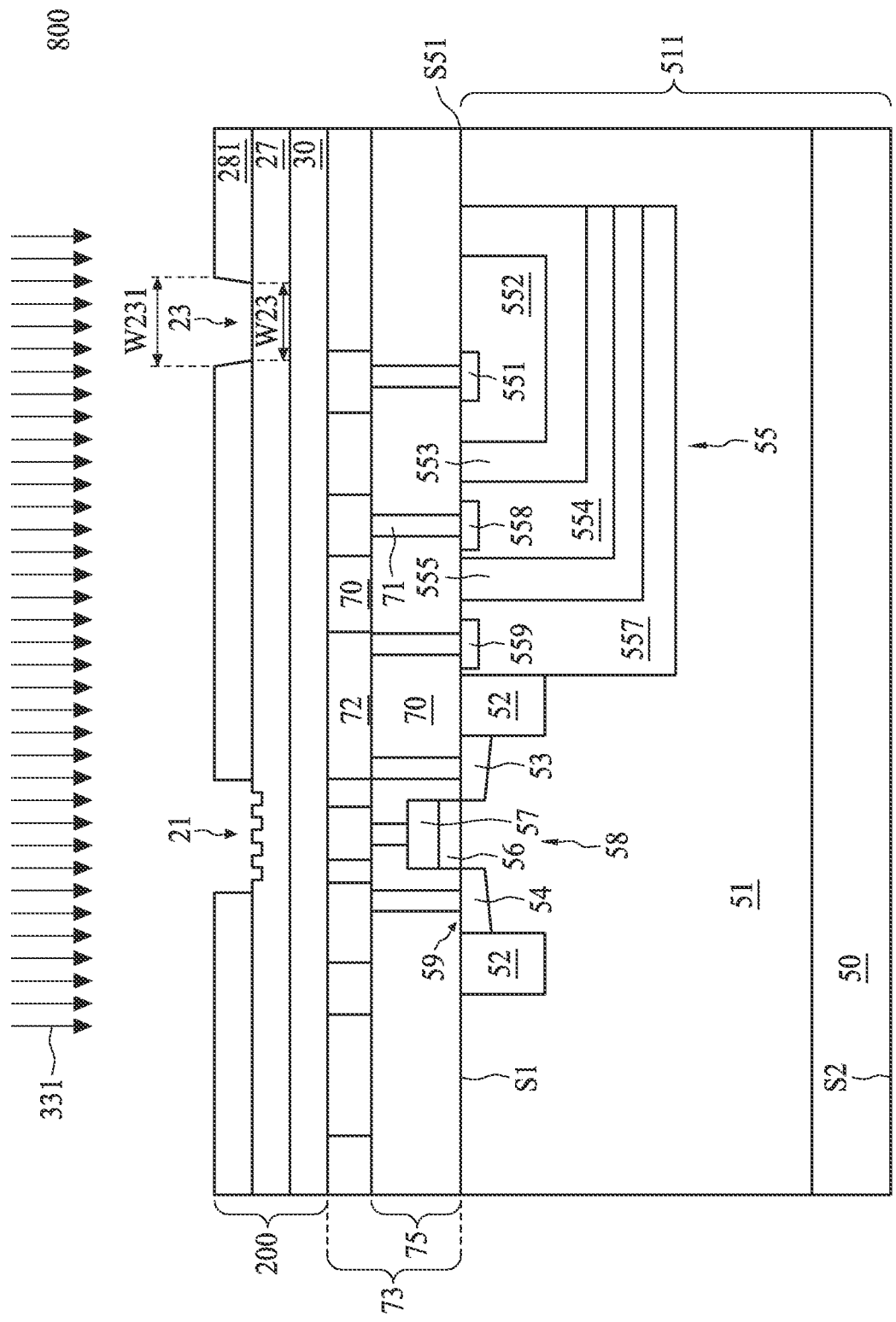

FIG. 29 shows a front side optical sensor 800. In some embodiments, instead of flipping the intermediate product upside down and forming a waveguide region 200 on a back side S2, as illustrated in FIG. 26, FIG. 29 demonstrate forming both the interconnection region 73 and the wave guide region 200 on the front side S1 of the semiconductive block 511. Compared to the optical sensor which utilizes external sensing device such as Photomultiplier Tube (PMT) or Charge Couple Devices (CCD), the front side optical sensor 800 described herein is a monolithic structure and provides a shorter distance between the sample emitting fluorescent light and the light sensing region. A better sensitivity can be expected.

The wave guide region 200 is formed on top of the interconnection region 73 such that the interconnection region 73 is on top of the light sensing region 55. The filter layer 30 is formed on top of the interconnection region 73. The core layer 27 is on top of the filter layer 30 by any suitable deposition operation. The core layer 27 can be a dielectric layer including any suitable dielectric material. The dielectric layer can guide the incident light such as to pass under the sample holding portion 23.

In FIG. 29, the core layer 27 is patterned to form the grating structure 21. The covering layer 281 is covered on top of the core layer 27. The covering layer 281 can be formed by depositing any suitable conductive material or metal oxide on top of the core layer 27. In some embodiments, the conductive material is made of aluminum and the metal oxide is made of aluminum dioxide.

In some other embodiments, the covering layer 281 is a cladding layer made of dielectric material. The covering layer 281 is patterned by any suitable lithographic operation such as the etching operation similar to the etching operation 331 in FIG. 29. The covering layer 281 is patterned to expose the grating structure 21 and to form the sample holding portion 23. The sample holding portion 23 can be patterned to possess a width W231 at a top of an opening and width W23 at a bottom of the opening. The width W23 is smaller than the wavelength of the incident light such as light 8. In some embodiments, the sample holding portion 23 is a nanowell.

Figure 30:
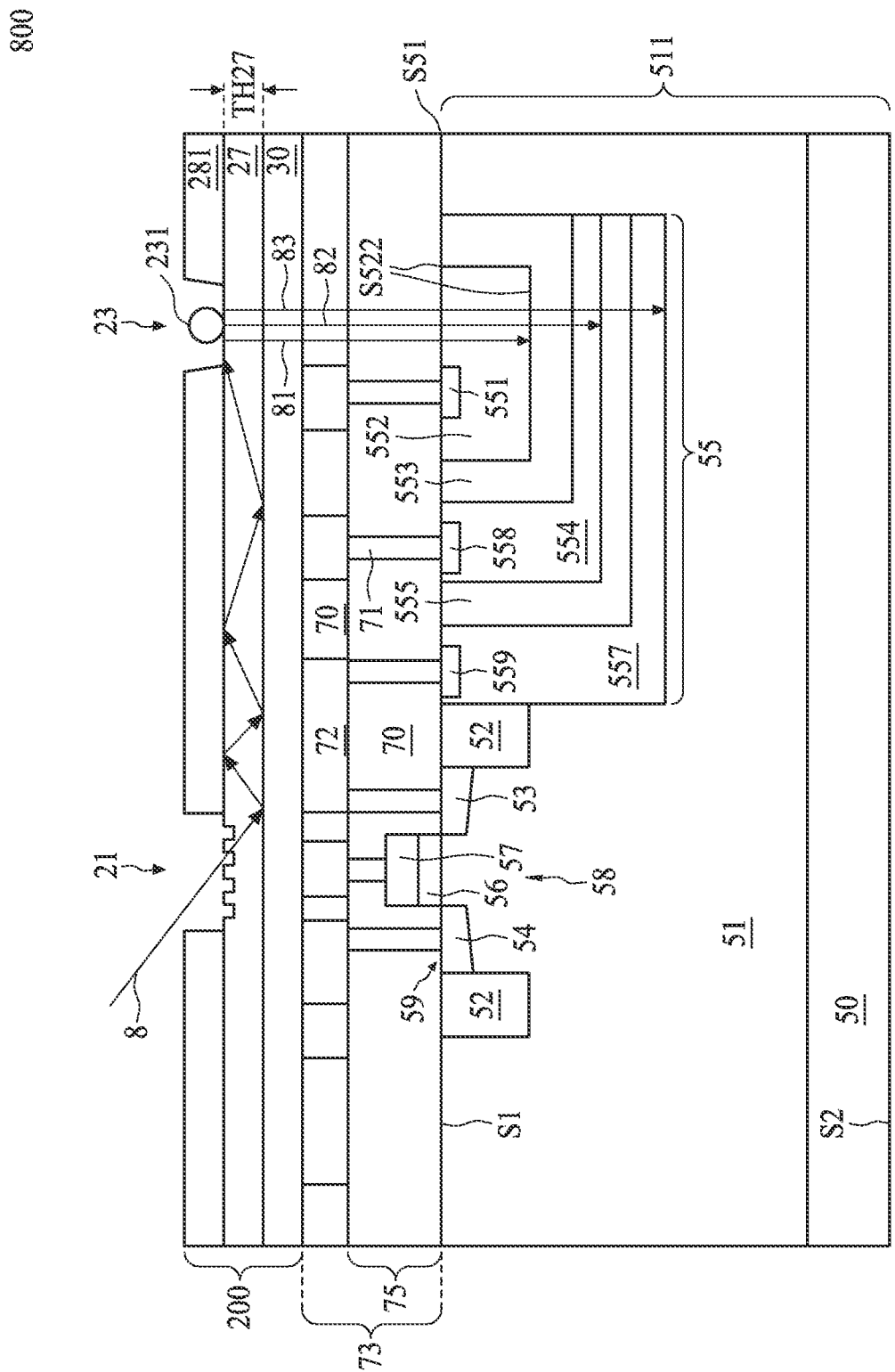
FIGS. 30-31 are cross-sectional views of optical sensors, in accordance with some embodiments of the present disclosure.

In FIG. 30, in some embodiments, the interconnection region 73 is above the front side S1 of semiconductive block 511. The interconnection region 73 electrically couples with the multi-junction photodiode of light sensing region 55. The multi-junction photodiode is in the semiconductive block 511. The multi-junction photodiode borders with the interconnection region 73 at the front side S1. The interconnection region 73 is between the multi-junction photodiode and the wave guide region 200.

The wave guide region 200 includes the core layer 27. The core layer 27 can be a dielectric layer to guide the incident light 8 from the grating structure 21 to the sample holding portion 23. The core layer 27 includes the grating structure 21 to direct the incident light such as the light 8 into the core layer 27. The dielectric layer of the core layer 27 includes a predetermined thickness TH27 around 150 nanometers plus about 5 to 10 percent. The Sample holding portion 23 can be the nanowell 23. The fluorescent light such as the light 81, 82, or 83 from the specimen 231 travels from the nanowell 23 to reach the light sensing region 55 through the dielectric layer 70 in the interconnection region 73.

The covering layer 281 can be the cladding layer including sample holding portion 23 to receive the specimen 231 such as a single molecule. The single molecule can absorb the incident light 8 and emit the fluorescent light 81, 82, or 83. In some other embodiments, the covering layer 281 can be the conductive layer on top of the core layer 27. The conductive layer includes the sample holding portion 23 to expose the core layer 27. The covering layer 281 includes an opening exposing the core layer 27 of the wave guide region 200. The opening includes a width smaller than a wavelength of the light 8.

The multi-junction photodiode bordered with the front side S1 can sense the fluorescent light 81, 82, or 83 from the wave guide region 200. The multi-junction photodiode includes a junction S522 capable of detecting emission lights such as the fluorescent light 81, 82, or 83. The junction S522 is in contact with the front side S1.

Figure 31:
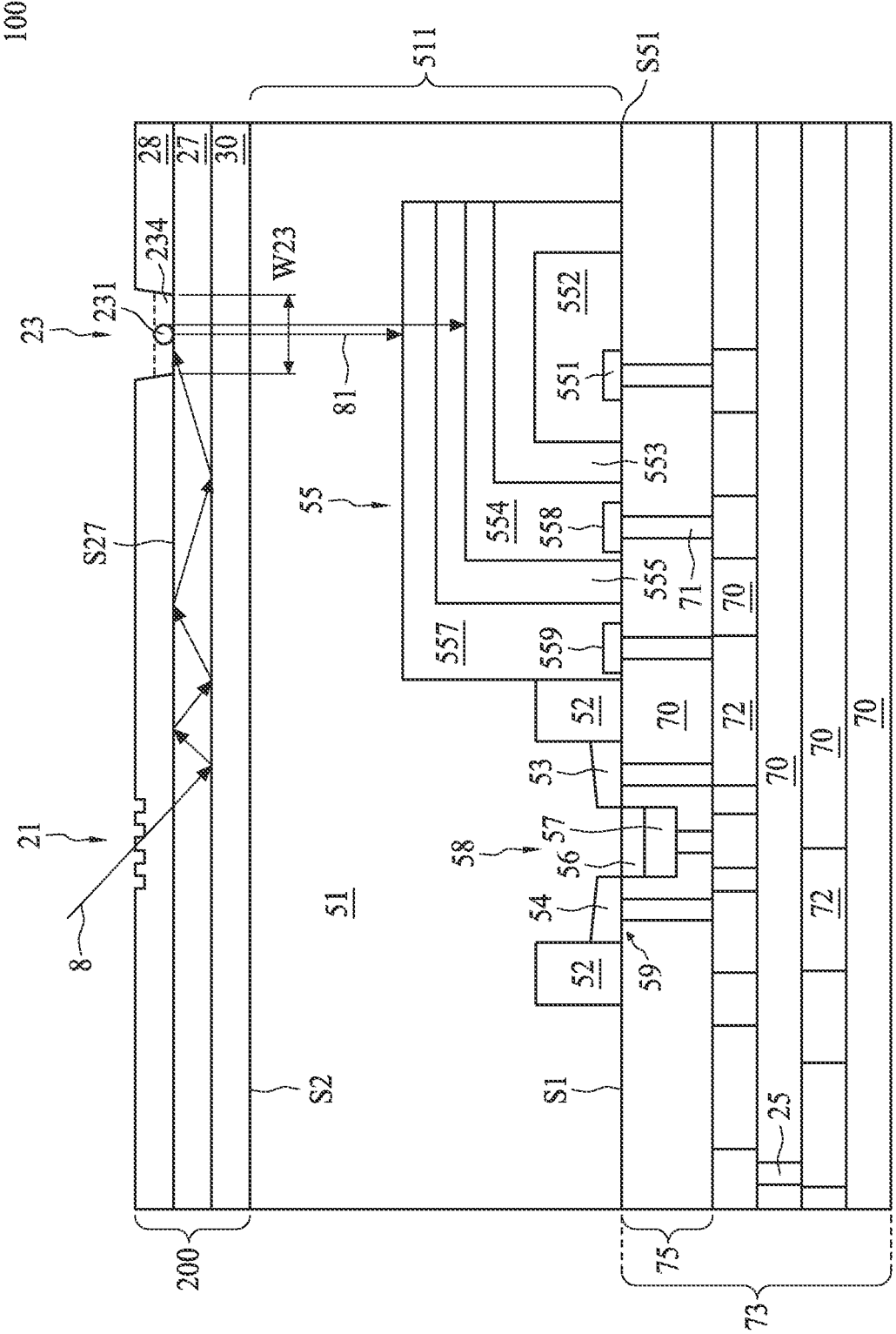

Referring to FIG. 31, FIG. 31 shows the optical sensor 100 with a wave guide region 200 in proximity to the back side S2 of the semiconductive block 511. In some embodiments, the optical sensor 100 can detect the fluorescent light such as the light 81 emitted from a single molecule specimen 231. Real time sequencing for a single molecule specimen 231 can be a parallelized single molecule DNA sequencing. Compared to the front side optical sensor 800 shown in FIG. 30, the optical sensor 100 is capable of detecting weaker light emitted from a single molecule specimen 231. For single molecule detection, one may need to prevent excitation light such as the light 8 from reaching the light sensing region 55 in order to enhance the signal-to-noise ratio. In a planar waveguide such as in the wave guide region 200, the core layer 27 includes a surface roughness of less than about 0.3 nm to reduce noises coming from a surface scattering of the excitation light propagating within the core layer 27. The sample holding portion 23 can receive a single molecule for analyzing.

In some embodiments, at least one sample holding portion 23 may be formed in at least the upper cladding layer 28. An upper opening of the sample holding portion 23 may be larger than a bottom of the sample holding portion 23. A shape of the sample holding portion 23 is not limited herein. For example, a horizontal cross section of the sample holding portion 23 may have a circular shape, an oval shape, a rectangular shape, a square shape, or a diamond shape.

Referring to FIG. 31, a size of the bottom of the sample holding portion 23 is variable. For example, the width W23 is the size of the bottom of the sample holding portion 23. The width W23 may be smaller than about a wavelength of the excitation light such as the light 8. In some embodiments, the width W23 may be smaller than about one-half, about one-quarter, or about one-eighth of the wavelength of the excitation light. As used herein, the width W23 may refer to a diameter or a greatest dimension of the sample holding portion 23 including a circular shape, an oval shape, or a rectangular shape. For the horizontal cross section of the sample holding portion 23 having a square or a diamond shape, the width W23 may be substantially equal to a length of a side of the shapes. In one embodiment, a diameter of the upper opening of the sample holding portion 23 may be about 0.5 μm to about 10 μm and the diameter of the bottom of the sample holding portion 23 may be about 10 to about 500 nm.

In some embodiments, angle of a sidewall S23 of the sample holding portion 23 relative to a direction perpendicular to the bottom of the sample holding portion 23 may be less than about 60 degree. Such a configuration may ensure that only one single molecule can enter a region near the bottom of the sample holding portion 23 and be detected.

In some embodiments, referring to FIG. 31, the sample holding portion 23 may extend through full thickness of the upper cladding layer 28. Some effective excitation zones such as the effective excitation zone 234 extends to the bottom of the sample holding portion 23.

In FIG. 31, for a planar waveguide including the sample holding portion 23, since the bottom end of the sample holding portion 23 is located right on the upper surface S27 of the core layer 27, a volume of the effective excitation zone 234 may be equal to the effective region of the evanescent field.

Figure 32:
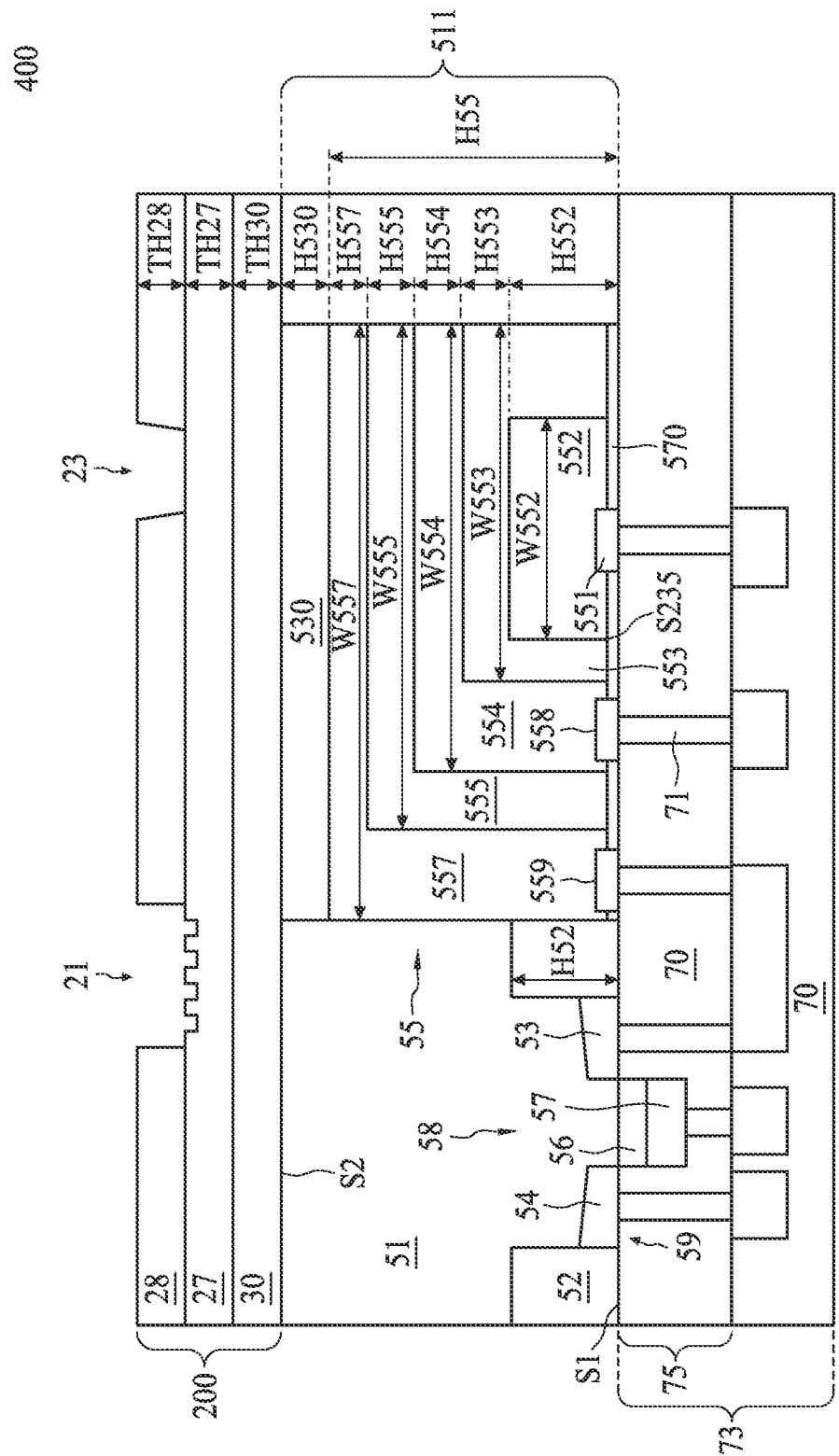
FIG. 32 is a cross-sectional view of an optical sensor, in accordance with some embodiments of the present disclosure.

FIG. 32 includes the optical sensor 400 similar to the optical sensor 100 in FIG. 2, except that in FIG. 32, the light sensing region 55 is bordered with the wave guide region 200. A bottom of filter layer 30 is in contact with a top of the light sensing region 55 in proximity to the back side S2. Alternatively, the light sensing region 55 is in proximity to the wave guide region 200 without direct contact. An additional semiconductor layer at a region 530 is disposed above the region 557. The region 530 includes a height H530 from the back side S2 to a top of the region 557. In some embodiments, the region 530 is a heavily doped region with a dopant concentration at least one order of magnitude greater than that of the region 555. In some embodiments, the region 530 includes a vertical portion (not shown in FIG. 32) and a horizontal portion. The horizontal portion is substantially parallel to the front side S1 or the back side S2, and the vertical portion is substantially orthogonal to the horizontal portion, positioning between the vertical portion of region 557 and the isolation region 52.

In some embodiments, the height H530 can be in a range of from about 0.27 µm to about 0.4 µm; the height H557 can be in a range of from about 0.5 µm to about 0.8 µm; the height H555 can be in a range of from about 0.2 µm to about 0.3 µm; the height H554 can be in a range of from about 0.4 µm to about 0.6 µm; the height H553 can be in a range of from about 0.4 µm to about 0.6 µm; and the height H552 can be in a range of from about 0.6 µm to about 0.9 µm.

In some embodiments, the regions 530, 555, and 553 include positive dopants such as boron. For example, the region 530 includes a peak doping concentration in a range of from about 8E18 atoms/cm$^3$ to about 2E19 atoms/cm$^3$. The region 555 includes a peak doping concentration in a range of from about 6E17 atoms/cm$^3$ to about 1E18 atoms/cm$^3$. The region 553 includes a peak doping concentration in a range of from about 2E17 atoms/cm$^3$ to about 5E17 atoms/cm$^3$. The doping concentration in region 555 can be greater than the doping concentration in region 553. In some embodiments, the regions 557, 554, and 552 include negative dopants such as phosphorus. The region 557 includes a peak doping concentration in a range of from about 4E16 atoms/cm$^3$ to about 1E17 atoms/cm$^3$. The region 554 includes a peak doping concentration in a range of from about 8E16 atoms/cm$^3$ to about 2E17 atoms/cm$^3$. The region 552 includes a doping concentration around 1E16 atoms/cm$^3$. The epitaxy region 51 includes a doping concentration at around 10E15 atoms/cm$^3$.

Some embodiments of the present disclosure provide an optical sensor. The optical sensor includes a semiconductive block including a front side and a back side. A wave guide region is over the back side of the semiconductive block. A wave guide region includes a core layer. The wave guide region is configured to guide an incident light. A light sensing region is in the semiconductive block. A light sensing region includes a multi-junction photodiode. The light sensing region is configured to sense emission lights.

In some embodiments of the present disclosure, the wave guide region includes an upper cladding layer and a lower cladding layer, and a ratio between thicknesses of the lower cladding layer and the upper cladding layer is from about 1 to about 2.

In some embodiments of the present disclosure, the multi-junction photodiode includes a first junction closest to the front side and a second junction furthest from the front side, and a distance from the first junction to the second junction is proximately from around 2 micrometers to around 3 micrometers.

In some embodiments of the present disclosure, the multi-junction photodiode includes a first horizontal junction closer to the front side than a second horizontal junction, and the first horizontal junction is smaller than the second horizontal junction.

In some embodiments of the present disclosure, the core layer includes a first refractive index and a cladding layer includes a second refractive index, and the second refractive index is smaller than the first refractive index.

In some embodiments of the present disclosure, the wave guide region includes a filter layer. The filter layer is disposed between the back side and the core layer.

In some embodiments of the present disclosure, the multi-junction photodiode includes a first junction closest to the front side; a second junction closest to the back side; and a third junction between the first junction and the second junction. A ratio of distances from the back side to the first junction, the second junction, and the third junction respectively is in a range of from about 4:1:2 to about 9:1:3.

In some embodiments of the present disclosure, the multi-junction photodiode includes a second junction disposed away from the back side by a first predetermined distance, and the first predetermined distance being in a range of from about 200 nm to about 500 nm.

In some embodiments of the present disclosure, the multi-junction photodiode includes a first junction disposed away from the back side by a second predetermined distance. The second predetermined distance is from about 2.5 µm to about 3 µm.

In some embodiments of the present disclosure, a cladding layer is over the core layer, and the cladding layer includes a nanowell.

In some embodiments of the present disclosure, a covering layer is over the core layer, the covering layer includes a metal or metal oxide.

In some embodiments of the present disclosure, a covering layer is over the core layer, and the covering layer includes aluminum or aluminum oxide.

Some embodiments of the present disclosure provide an optical sensor. The optical sensor includes a semiconductive block including a front side. A wave guide region includes a core layer. The wave guide region is configured to guide an incident light. A light sensing region is configured to sense an emission light. An interconnection region above the front side. The interconnection region is configured to couple with the light sensing region. The interconnection region is between the light sensing region and the wave guide region.

In some embodiments of the present disclosure, the wave guide region includes a cladding layer.

In some embodiments of the present disclosure, the cladding layer includes a nanowell.

In some embodiments of the present disclosure, the cladding layer includes a sample holding portion configured to receive a specimen including a single molecule.

In some embodiments of the present disclosure, the core layer includes a grating structure.

In some embodiments of the present disclosure, the core layer includes a predetermined thickness around 150 nanometers plus about 5 to 10 percent.

In some embodiments of the present disclosure, the light sensing region includes a multi junction photodiode, and the multi-junction photodiode including a junction in contact with the front side.

In some embodiments of the present disclosure, a covering layer is on top of the wave guide region. The covering layer includes an opening exposing the wave guide region, and the covering layer including metal or metal oxides.

In some embodiments of the present disclosure, the opening includes a width smaller than a wavelength of the incident light.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An optical sensor, comprising:
   a semiconductive block comprising a front side and a back side;
   an interconnection region positioned below the front side;
   a wave guide region over the back side of the semiconductive block, comprising:
      a core layer;
      a cladding layer surrounding the core layer; and
      a grating structure above the core layer, configured to guide an incident light of a first wavelength into the core layer;
      a filter layer under the cladding layer, wherein the filter layer is opaque to the incident light having the first wavelength and allowing a fluorescent light of a second wavelength to pass through;
   a light sensing region in the semiconductive block, comprising a multi junction photodiode, the light sensing region being configured to sense an emission light and the light sensing region comprising:
      a first region configured to absorb the emission light; and
      a doping region, between the first region and the interconnect region, being contact with the interconnection region;
   an isolation layer; and
   a transistor including a drain region in the semiconductive block
   wherein the drain region is isolated from the multi junction photodiode by the isolation structure.

2. The optical sensor of claim 1, wherein the cladding layer comprises an upper cladding layer and a lower cladding layer, and a ratio between thicknesses of the lower cladding layer and the upper cladding layer is from about 1 to about 2.

3. The optical sensor of claim 1, wherein the multi junction photodiode comprises a first junction closest to the front side and a second junction furthest from the front side, and a distance from the first junction to the second junction is proximately from around 2 micrometers to around 3 micrometers.

4. The optical sensor of claim 1, wherein the multi junction photodiode comprises a first horizontal junction closer to the front side than a second horizontal junction, and the first horizontal junction being smaller than the second horizontal junction.

5. The optical sensor of claim 1, wherein the core layer comprises a first refractive index and the cladding layer comprises a second refractive index, and the second refractive index being smaller than the first refractive index.

6. The optical sensor of claim 1, wherein the filter layer is disposed between the back side and the core layer.

7. The optical sensor of claim 1, wherein the multi junction photodiode comprises:
   a first junction closest to the front side;
   a second junction closest to the back side; and
   a third junction between the first junction and the second junction,
   wherein a ratio of distances from the back side to the first junction, the second junction, and the third junction respectively is in a range of from about 4:1:2 to about 9:1:3.

8. The optical sensor of claim 1, wherein the multi junction photodiode comprises a second junction disposed away from the back side by a first predetermined distance, and the first predetermined distance being in a range of from about 200 nm to about 500 nm.

9. The optical sensor of claim 8, wherein the multi junction photodiode comprises a first junction disposed away from the back side by a second predetermined distance, and the second predetermined distance being from about 2.5 µm to about 3 µm.

10. The optical sensor of claim 1, wherein the cladding layer comprises a nanowell.

11. The optical sensor of claim 1, further comprising a covering layer over the core layer, the covering layer comprising a metal or metal oxide.

12. The optical sensor of claim 1, further comprising a covering layer over the core layer, the covering layer comprising aluminum or aluminum oxide.

13. The optical sensor of claim 1, wherein the cladding layer comprises an upper cladding layer and a lower cladding layer, and the grating structure being in the upper cladding layer.

* * * * *